(12) United States Patent
Wang

(10) Patent No.: US 12,277,684 B2
(45) Date of Patent: Apr. 15, 2025

(54) K-SPACE BASED METHOD FOR REDUCING NOISE AND DOSE OF RADIATION OR CONTRAST FOR PERFUSION IMAGING

(71) Applicant: HURA IMAGING, INC, Calabasas, CA (US)

(72) Inventor: Danny J J Wang, Calabasas, CA (US)

(73) Assignee: HURA IMAGING, INC, Calabasas, CA (US)

(*) Notice: Subject to any disclaimer, the term of this patent is extended or adjusted under 35 U.S.C. 154(b) by 387 days.

(21) Appl. No.: 17/574,988

(22) Filed: Jan. 13, 2022

(65) Prior Publication Data

US 2022/0180482 A1   Jun. 9, 2022

Related U.S. Application Data

(63) Continuation of application No. PCT/US2020/045285, filed on Aug. 6, 2020.
(Continued)

(51) Int. Cl.
G06T 5/00 (2024.01)
G06T 5/70 (2024.01)
G06T 11/00 (2006.01)

(52) U.S. Cl.
CPC .............. *G06T 5/70* (2024.01); *G06T 11/006* (2013.01); *G06T 2207/10081* (2013.01); *G06T 2207/10088* (2013.01)

(58) Field of Classification Search
CPC ......... G06T 11/006; G06T 11/00; G06T 5/70; G06T 5/00; G06T 5/002; G06T 2207/10081; G06T 2207/10088
See application file for complete search history.

(56) References Cited

U.S. PATENT DOCUMENTS

| | | |
|---|---|---|
| 2003/0184291 A1 | 10/2003 | Rehwald |
| 2007/0009080 A1 | 1/2007 | Mistretta |
| 2018/0132800 A1* | 5/2018 | Wang ........................ A61B 6/06 |

FOREIGN PATENT DOCUMENTS

WO    2021030157    2/2021

OTHER PUBLICATIONS

Martin, Thomas et al.,"Low-Dose CT perfusion with projection view sharing", 101, Med. Phys. 45(1), Jan. 2018, 0094-2405/2018/45(1)/101/13, 2017 American Association of Physicsts in Medicine, pp. 101-113.

(Continued)

*Primary Examiner* — Tuan H Nguyen
(74) *Attorney, Agent, or Firm* — O'BANION & RITCHEY LLP; John P. O'Banion

(57) ABSTRACT

Reducing noise and dose (radiation or contrast) for perfusion imaging in Computed Tomography Perfusion (CTP), Positron Emission Tomography (PET), Single Photon Emission Computed Tomography (SPECT), and Magnetic Resonance Imaging (MRI) medical scanning devices by using a k-space based method. The time sequence of images from the scanner data set is converted as necessary, such as using a 2D Fast Fourier Transform (FFT), into a k-space having multiple timeframes. View-shared averaging is performed to reduce noise and preserve spatial and temporal resolutions of CTP, PET, SPECT and MRI data by progressively increasing the number of time frames for view-shared averaging for more distant regions of "k-space", before converting the data, such as through a 2D FFT into a time sequence of noise reduced images.

8 Claims, 13 Drawing Sheets

Related U.S. Application Data

(60) Provisional application No. 63/038,071, filed on Jun. 11, 2020, provisional application No. 62/884,953, filed on Aug. 9, 2019.

(56) References Cited

OTHER PUBLICATIONS

Martin, Thomas et al., "Low Dose CT Perfusion with Projection View Sharing", HHS Public Access, Author manuscript, Med Phys. Jan. 2018, 45(1): 101-113, doi:10.1002/mp.12640, pp. 1-27.

Prachi, Pandit et al., "Whitepaper—CT Neuro Perfusion in ischemic stroke management: whole brain dynamic imaging with automated perfusion analysis", Published by Siemens Medical Solutions USA, Inc.—Order No. CT-20-NAM-1307—Online Sep. 2020, Siemens Medical Solutions USA, Inc. 2020, pp. 1-18.

ISA/US, United States Patent and Trademark Office (USPTO), International Search Report and Written Opinion issued Dec. 22, 2020, related PCT international application No. PCT/US2020/045285, pp. 1-14, with claims searched, pp. 15-22.

State Intellectual Property Office of the People's Republic of China, the first office action issued Oct. 31, 2024, related Chinese application No. 202080058993.1, Chinese-language document, pp. 1-21, English-language translation, pp. 22-46, claims examined, pp. 47-54.

\* cited by examiner

K-SPACE BASED METHOD FOR REDUCING NOISE AND DOSE OF RADIATION OR CONTRAST FOR PERFUSION IMAGING

CROSS-REFERENCE TO RELATED APPLICATIONS

This application claims priority to, and is a 35 U.S.C. § 111(a) continuation of, PCT international application number PCT/US2020/045285 filed on Aug. 6, 2020, incorporated herein by reference in its entirety, which claims priority to, and the benefit of, U.S. provisional patent application Ser. No. 63/038,071 filed on Jun. 11, 2020, incorporated herein by reference in its entirety, and which also claims priority to, and the benefit of, U.S. provisional patent application Ser. No. 62/884,953 filed on Aug. 9, 2019, incorporated herein by reference in its entirety. Priority is claimed to each of the foregoing applications.

The above-referenced PCT international application was published as PCT International Publication No. WO 2021/030157 A1 on Feb. 18, 2021, which publication is incorporated herein by reference in its entirety.

STATEMENT REGARDING FEDERALLY SPONSORED RESEARCH OR DEVELOPMENT

This invention was made with Government support under R41-EB024438, awarded by the National Institutes of Health. The Government has certain rights in the invention.

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to medical imaging, and more particularly to K-space weighted image averaging (KWIA) for reducing image noise and/or dose (e.g., radiation or contrast agent).

2. Background Discussion

A number of medical imaging techniques have been developed and applied to evaluate brain hemodynamics, including computed tomography perfusion (CTP), positron emission tomography (PET), single photon emission computed tomography (SPECT), and magnetic resonance imaging (MRI). These techniques use different tracers, such as radioactive or non-radioactive, endogenous or exogenous, diffusible or non-diffusible, and derive hemodynamic parameters, such as cerebral blood flow (CBF) and/or cerebral blood volume (CBV) based on kinetic modeling of the dynamic time-activity curves in each imaging modality.

However, image noise issues arise with these current image processing techniques, and in addition these techniques often fail to provide satisfactory results at lower dose levels.

Accordingly, a need exists for an enhanced image processing technique which reduces image noise problems and can be applied even at lower doses of radiation or contrast agents. The present disclosure fulfills that need and provides additional benefits over previous technologies.

BRIEF SUMMARY

By way of example, and not of limitation, this disclosure describes a system and method, termed "K-space Weighted Image Average" (KWIA), for reducing noise and dose of radiation and/or contrast agent, for perfusion imaging using Computed Tomography Perfusion (CTP), Positron Emission Tomography (PET), Single Photon Emission Computed Tomography (SPECT), and Magnetic Resonance Imaging (MRI). In one embodiment, KWIA uses Fourier space—equivalent to k-space in MRI-based processing to reduce the noise of CTP, PET, SPECT, and MRI scans while maintaining temporal and spatial resolution of the image and not requiring any modification to the existing scanner or lengthy computation time.

In at least one embodiment, low-dose computed tomography (CT) images are acquired. The low doses are achieved in these examples by reducing X-ray tube current or tube voltage or both.

In at least one embodiment, KWIA is applied to standard or reduced dose CT to reduce noise and enhance image contrast.

In at least one embodiment, PET and SPECT images are acquired with a reduced dose of radioactive tracers.

In at least one embodiment, KWIA is applied to PET and SPECT images with standard or reduced doses of radioactive tracers to reduce noise and enhance image contrast.

In at least one embodiment, Dynamic Susceptibility Contrast (DSC) MRI images are acquired with a reduced dose of contrast agent.

In at least one embodiment, KWIA is applied to DSC MRI with standard or reduced dose of contrast agent to reduce noise and enhance image contrast.

In at least one embodiment, Arterial Spin Labeling (ASL) MRI images are acquired with a reduced imaging time.

In at least one embodiment, KWIA is applied to ASL MRI with standard or reduced imaging time to reduce noise and enhance image contrast.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

Figure 7:
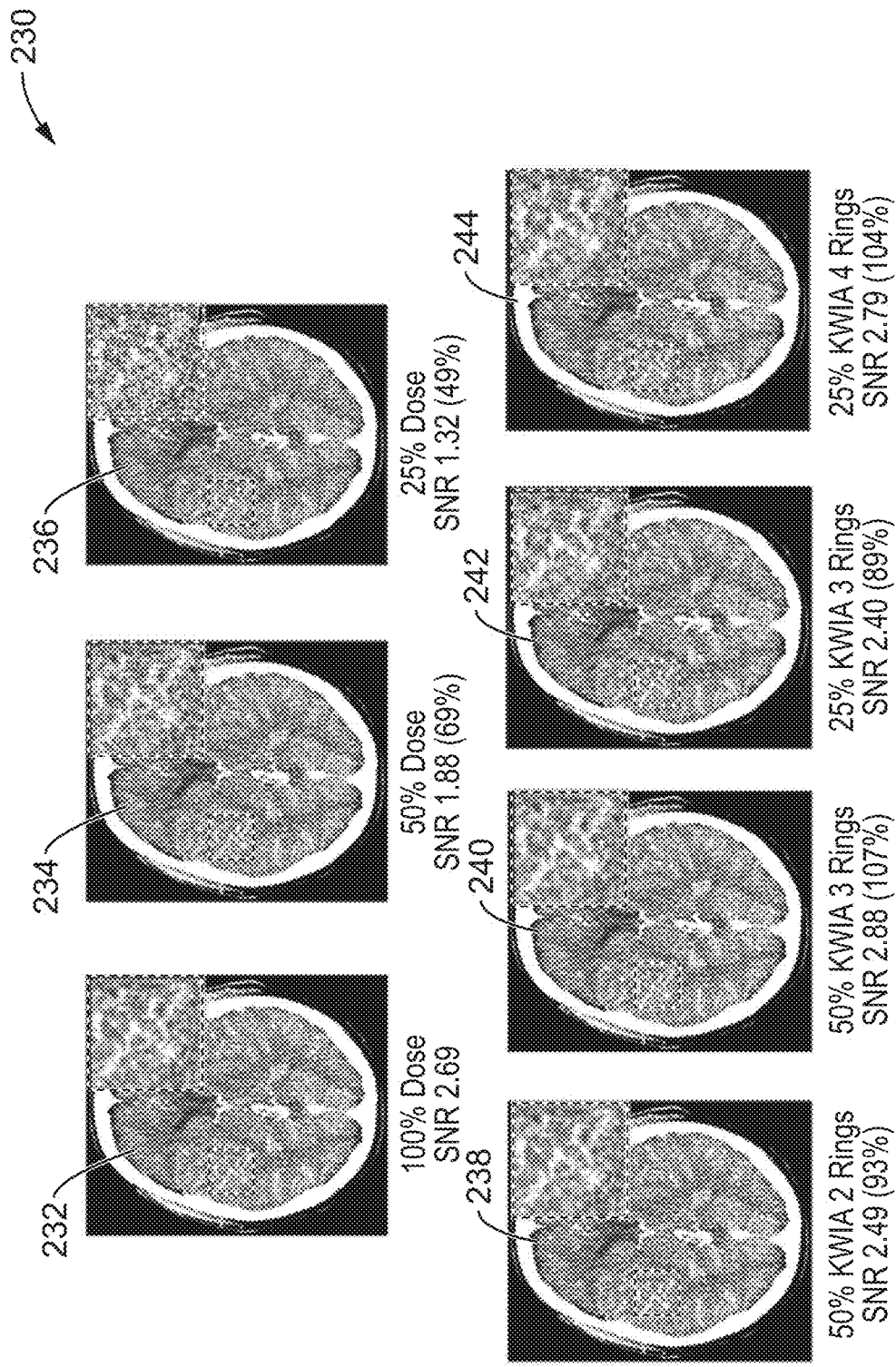
Figure 8A:
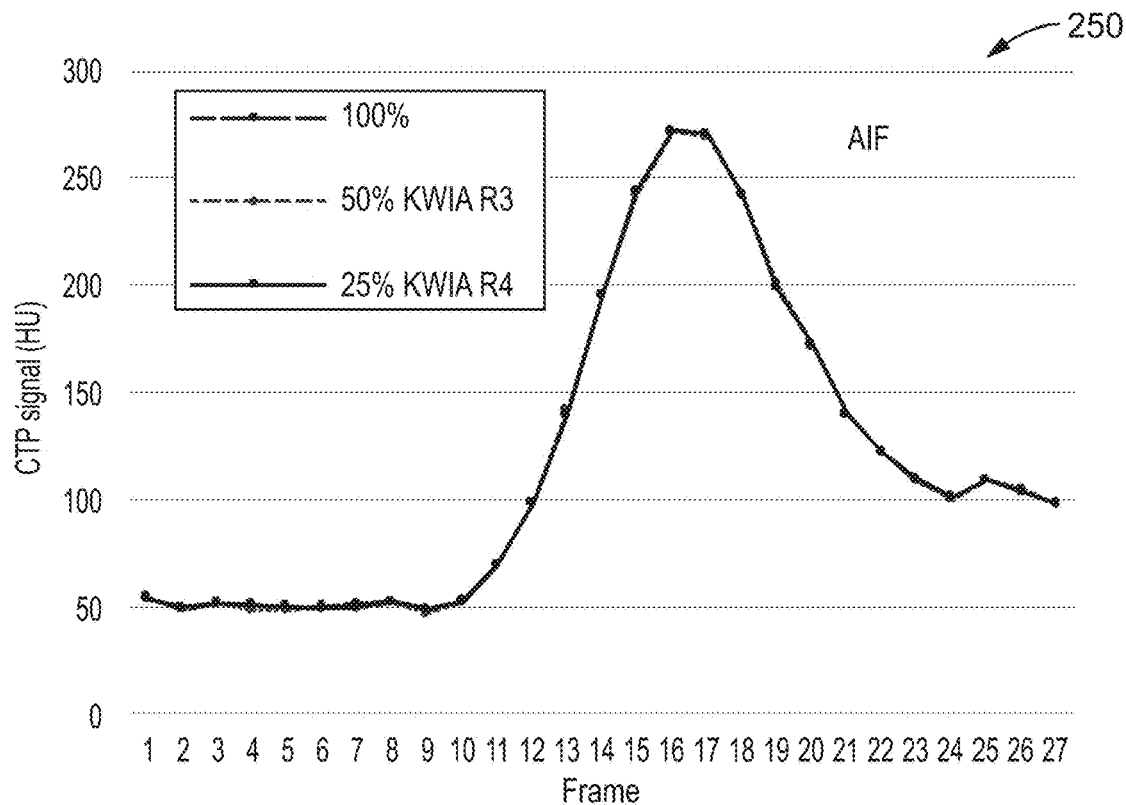
Figure 8B:
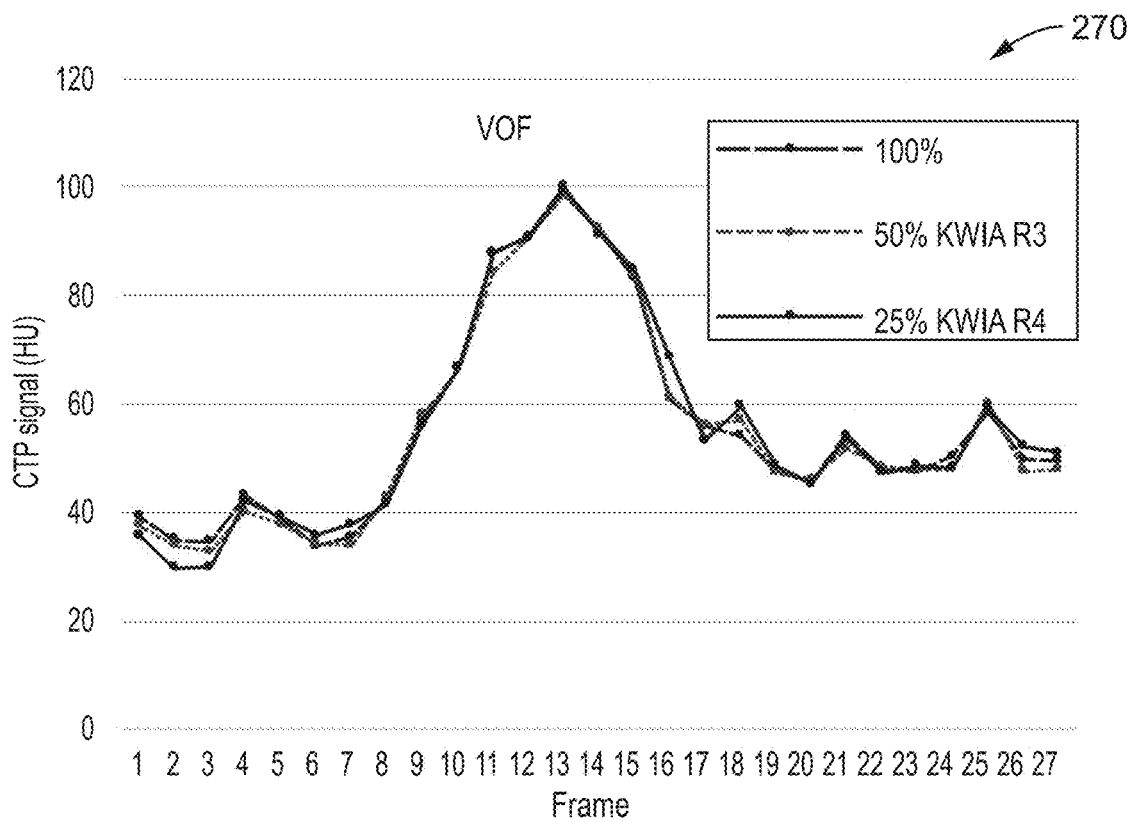
Figure 8C:
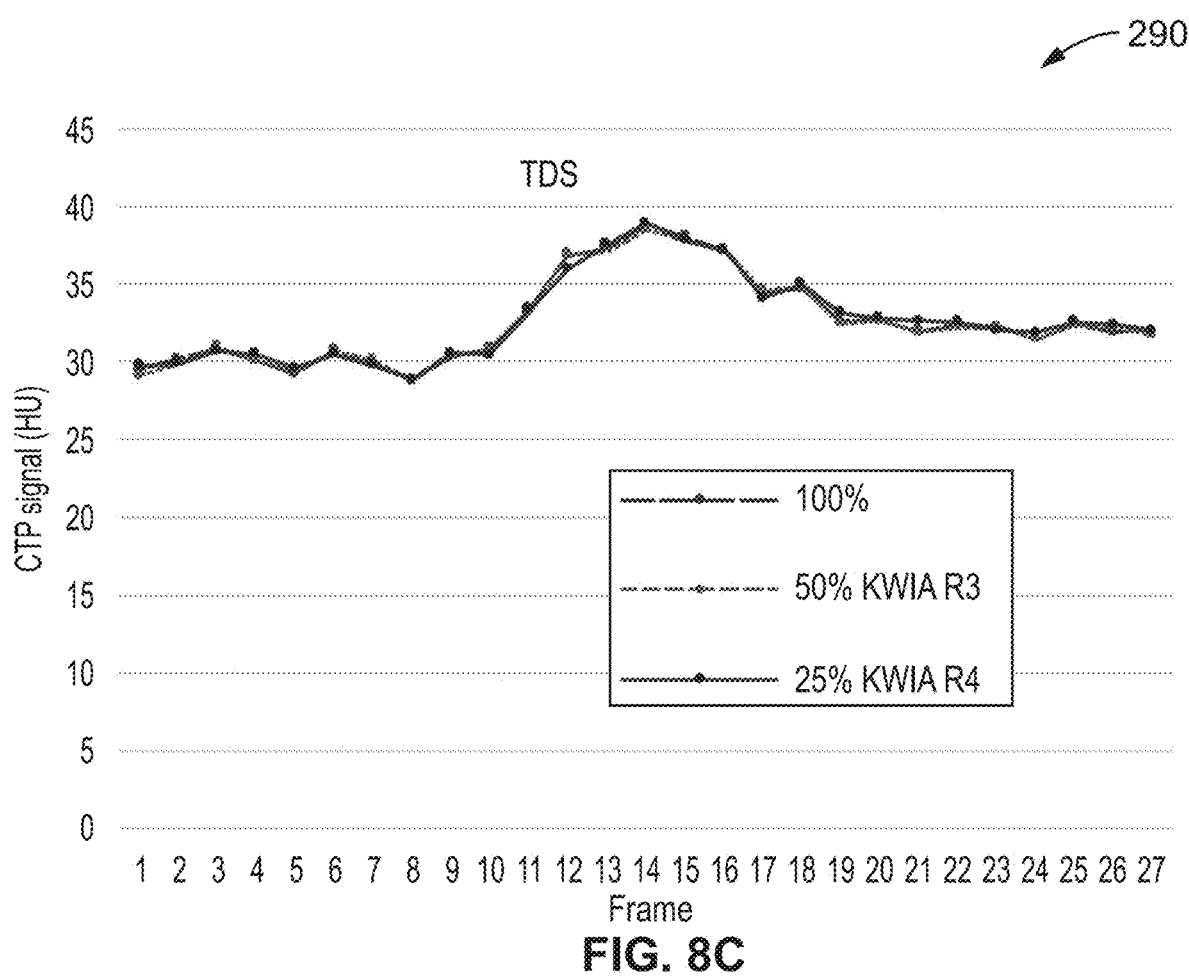
Figure 8D:
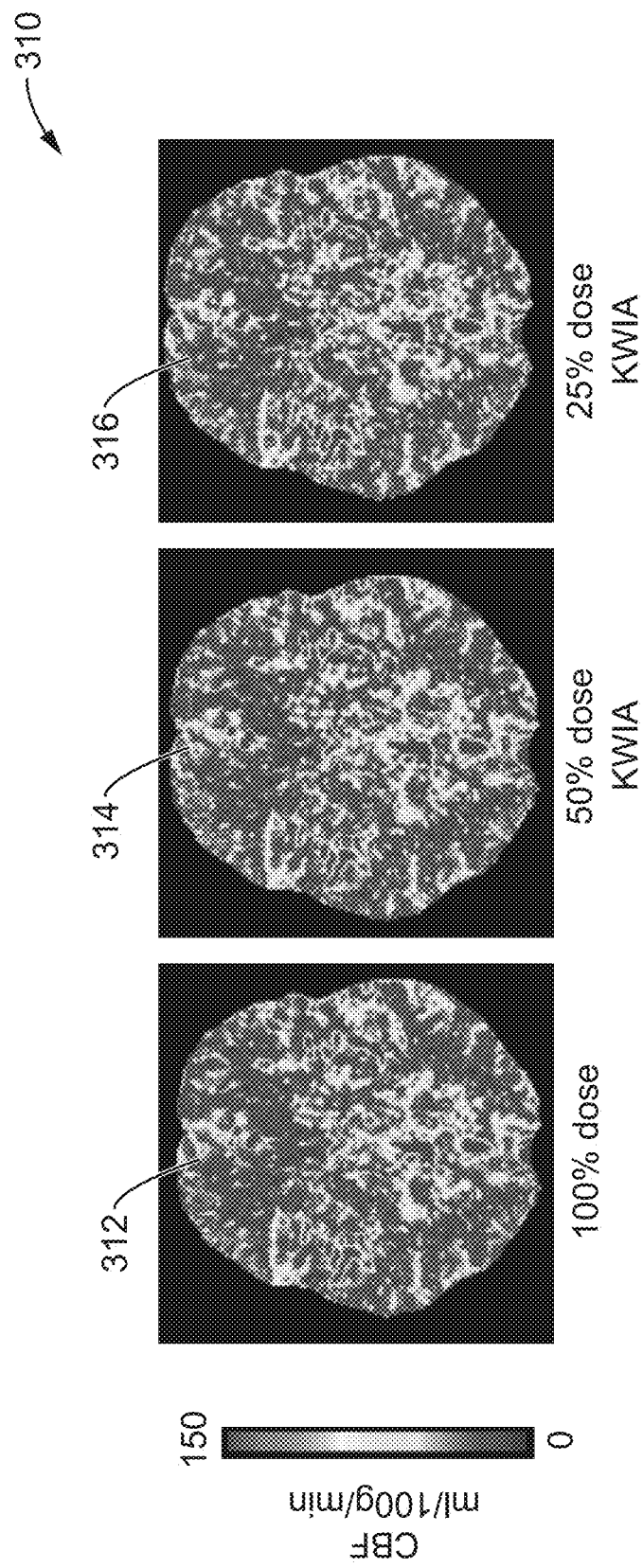

FIG. 7 are KWIA reconstruction images comparing clinical CTP data at 100% dose and simulated images at 50% and 25% doses respectively, with KWIA reconstructions with 2, 3 and 4 rings according to at least one embodiment of the present disclosure.

FIG. 8A through FIG. 8D are plots and KWIA reconstructed images of arterial input function (AIF), venous outflow function (VOF), tissue density signal (TDS), and cerebral blood flow (CBF) maps according to at least one embodiment of the present disclosure.

Figure 9:
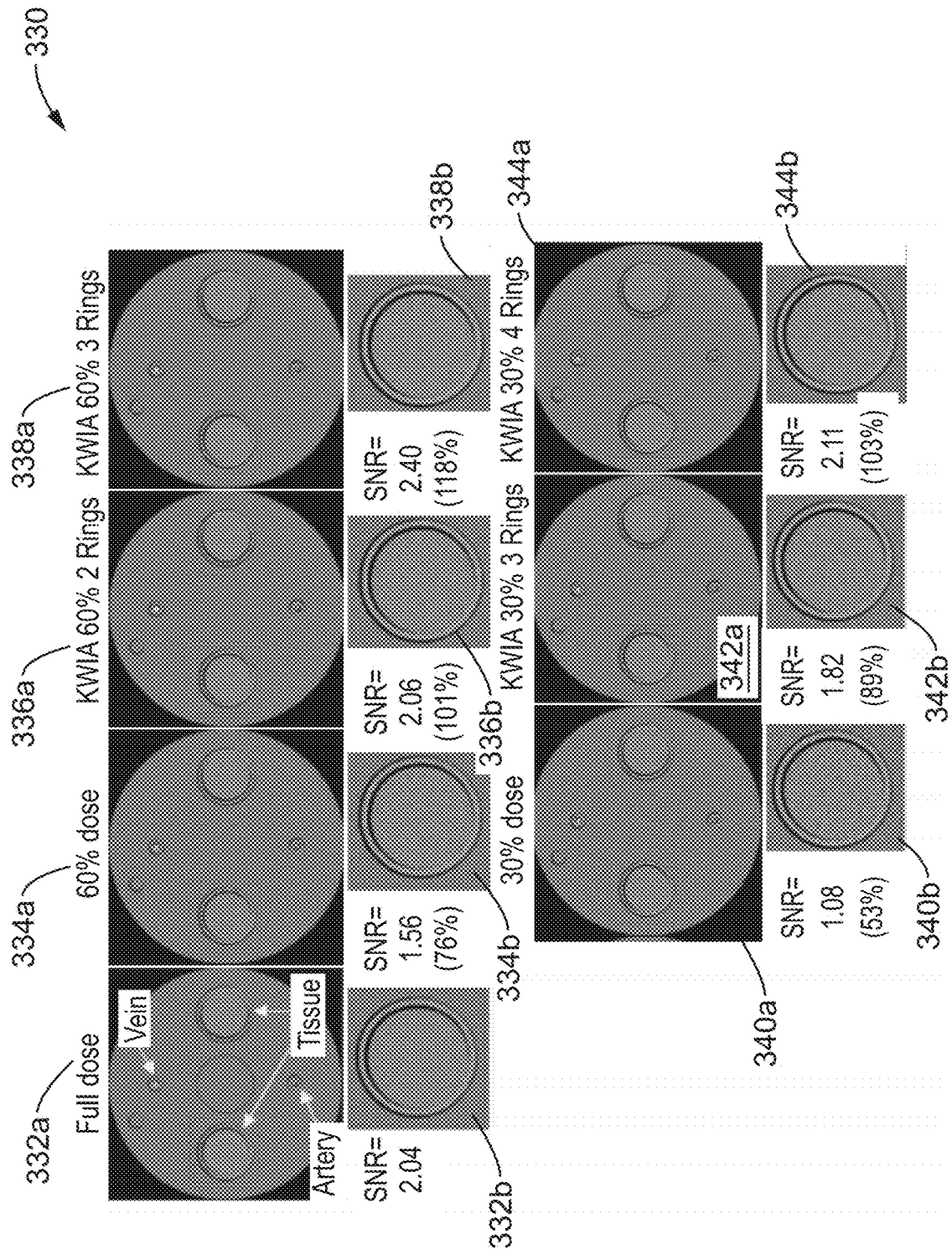

FIG. 9 are image comparisons between CTP phantom images acquired with real 100%, 60% and 30% dose, as well as 60% and 30% dose scans reconstructed using KWIA with 2, 3 and 4 rings according to at least one embodiment of the present disclosure.

Figure 10:
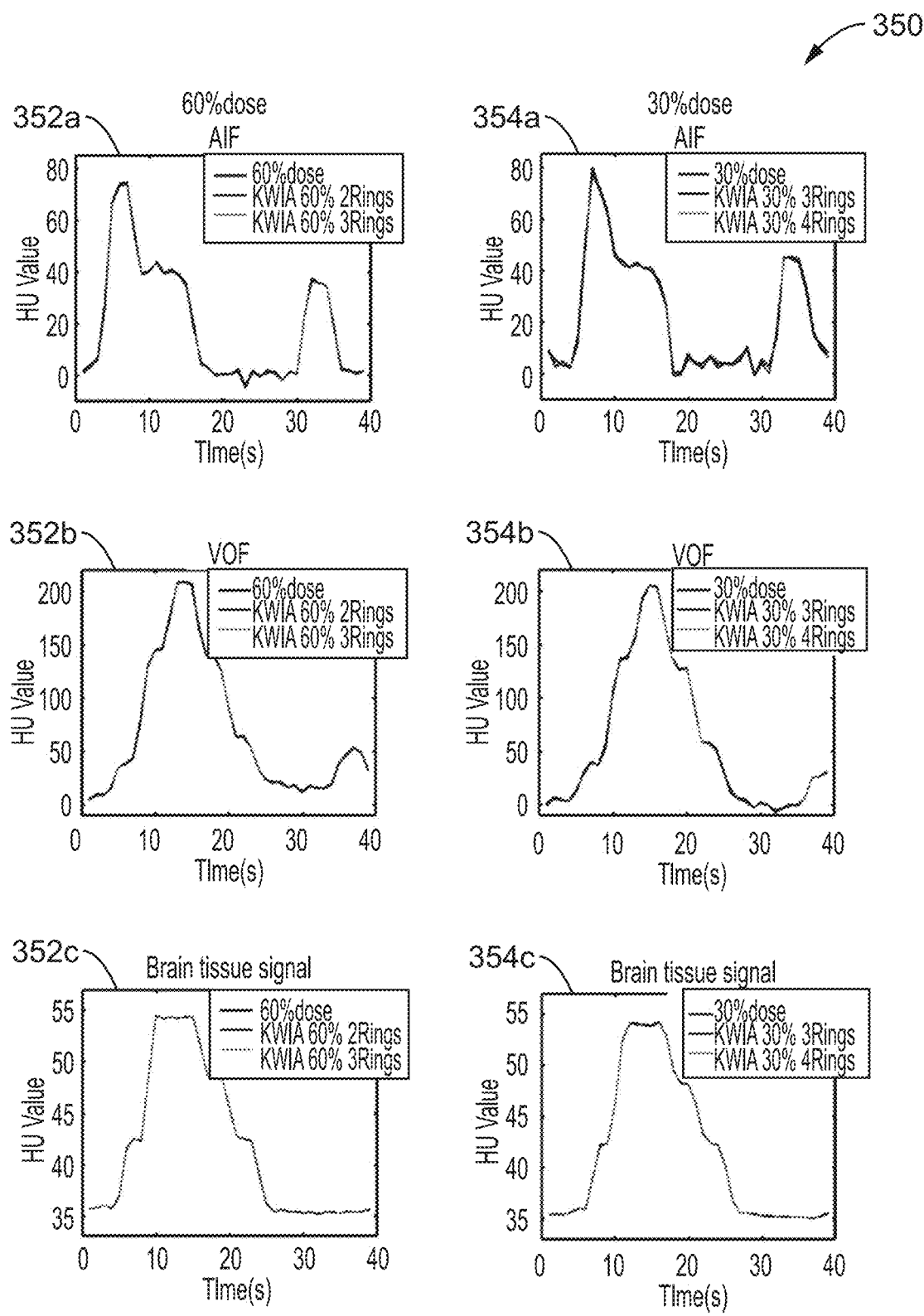

FIG. 10 are plots of arterial input function (AIF), venous outflow function (VOF) and tissue signals of 60% and 30% dose CTP phantom data reconstructed with KWIA methods according to at least one embodiment of the present disclosure.

DETAILED DESCRIPTION

1. Introduction

A novel k-space based method is described for reducing noise and/or dose of radiation or contrast agent for perfusion imaging for various medical imaging techniques including computed tomography perfusion (CTP), positron emission tomography (PET), single photon emission computed tomography (SPECT), and magnetic resonance imaging (MRI).

CT brain perfusion (CTP) is a widely used imaging technique for the evaluation of hemodynamic changes in stroke and cerebrovascular disorders. CTP is included in the American Heart Association (AHA) guideline for acute stroke imaging, to distinguish infarct core from penumbra brain tissue to aid in decision making for recanalization therapy. CTP is also used for other neurological disorders such as traumatic brain injury and brain tumor. In a typical CTP scan, a dataset of time-resolved CT images is acquired over the scan duration (~1 min) to track the passage of the contrast bolus through the intracranial vasculature. The contrast enhancement of the tissue over time is depicted by the time density curve (TDC), and multiple perfusion parameters such as cerebral blood flow (CBF), cerebral blood volume (CBV), mean transit time (MTT), can be derived from the TDC information. The repeated CT scans that are performed on the same brain region during the passage of a contrast bolus result in exposing a patient to high radiation doses. This has been raised as a major concern by the FDA, especially when multiple successive CTP scans are performed on the same patient, for example when monitoring reperfusion following recanalization.

Although dose reduction techniques such as reduction of tube current and/or voltage have been applied to CTP, the resultant radiation dose of existing CTP scans (greater than or equal to approximately 200 mGy) is still more than 3 times higher than that of a standard head CT. According to the ALARA (As Low As Reasonably Achievable) principle and AAPM (American Association of Physicists in Medicine) guidelines, currently a typical clinical CTP scan uses a reduced tube voltage of 80 kV with a relatively low tube current of 150 mAs, and a temporal sampling rate of 1 image every 1 to 2 s. As a result, the noise level in CTP images is much higher than that of standard CT images, especially in larger patients due to reduced penetration of the X-ray beam. The noise level of CTP images will also affect the accuracy of CTP quantification, as shown by previous studies. Noise reduction techniques, such as iterative reconstruction (IR) can be applied to CTP images to reduce noise, which is the current industry standard. However, IR methods often yield blotchy image appearance and require longer computational time. Although the application of IR in standard CT scans has been improving due to enhanced computational power, the application of iterative reconstruction (IR) techniques in CTP is very limited due to the high complexity and computational burden for processing multiple CTP images that impairs clinical workflow.

Positron emission tomography (PET) provides tomographic images of quantitative parameters describing various aspects of brain hemodynamics, including CBF, CBV, oxygen extraction fraction (OEF), metabolic activity of tissues, and neurotransmission processes and so forth. PET uses different radioactive tracers labeled with positron emitting radioisotopes to probe different biological processes of interest. The typical PET tracer used for CBF measurement is $H_2^{15}O$ which is administered by intravenous injection followed by a scan of approximately 2-minutes, within a time series of PET images being taken. An arterial blood sampling measurement is performed concurrently with PET scanning which serves as an arterial input function (AIF), and quantitative CBF maps can be calculated by applying the Kety-Schmidt model on the time series of PET images.

Single photon emission computed tomography (SPECT) is an imaging procedure in which a radioactive tracer tagged with an isotope is injected into a patient's vein. The isotope emits photons which are detected and recorded to form an image of the distribution of the radiotracer in the brain and body. Dynamic SPECT is a technique that uses tracers to measure perfusion and metabolism in the brain and body organs. Similar to PET, kinetic model-based analysis of a time series of dynamic reconstructed SPECT images allows for the quantitation (performing quantitative analysis upon) physiological parameters such as CBF. However, the development and use of kinetic analysis in dynamic PET and SPECT applications have been limited by the low sensitivity and low signal-to-noise ratio (SNR) due to the limited time window for photon emission of each time frame of PET/SPECT images. Although direct parametric reconstruction methods have been proposed for direct estimation of pharmacokinetic information from raw emission data (without reconstructing time series of images), these methods rely on specific assumptions that need to be validated in clinical practice.

Dynamic susceptibility contrast (DSC) MRI relies on the measurement of dynamic MRI signal changes during the first pass of an exogenous tracer through the capillary bed. Fast imaging techniques such as echo planar imaging are used to acquire a time series of MR images during 1-2 minutes following the intravenous injection of a bolus of gadolinium based contrast agent (GBCA). DSC relies on the application of the indicator dilution theory and its variant that accounts for blood-brain barrier (BBB) rupture to estimate hemodynamic parameters such as Cerebral Blood Flow (CBF), Cerebral Blood Volume (CBV), and Mean Transit Time (MTT). DSC MRI has been widely used for the evaluation of hemodynamic parameters in cerebrovascular disorders, brain tumors, and similar situations; however, the use of GBCAs is limited in patients with renal dysfunction due to the concern of nephrogenic systemic fibrosis (NSF). Studies have also demonstrated GBCA depositions in the dentate nucleus (DN) and globus pallidus (GP) in patients receiving repeated injections of GBCAs. While it is preferable to use a reduced dose of GBCA, the sensitivity of DSC MRI suffers since the change of relaxation rate (delta R2*) is proportional to the dose of GBCA.

Arterial spin labeled (ASL) MRI provides quantitative measurement of CBF by using magnetically labeled arterial blood water as an endogenous tracer, without the use of exogenous contrast agents or radioactive tracers. By employing ASL measurements at multiple post-labeling delays, multiple hemodynamic parameters can be estimated including CBF, arterial transit time (ATT) and arterial cerebral blood volume (aCBV) based on the tracer kinetic model. ASL is appealing for pediatric imaging, pregnant women and subjects with renal dysfunction. However, the major drawback of ASL is the low SNR since the labeled blood signal is less than 1% of the brain tissue signal and the label relaxes with the T1 of blood (1-2 sec) during the transit from the labeling region to the brain tissue of interest. As a result, lengthy scan times or repeated measurements are required to improve SNR and reliability of ASL MRI.

In the past few years, deep learning (DL) techniques have been explored for reducing the noise of CT, PET, MRI. It should be appreciated that DL is a machine learning method using neural network structures to provide predictive analytic outputs from a given a set of inputs. The "deep" usually refers to these neural networks having a higher number of hidden layers, thus the depth of the network is increased. The reduced noise achieved by DL allows the use of reduced X-ray radiation in CTP, as well as reduced dose of radioactive tracers in PET/SPECT, GBCAs in DSC MRI and reduced scan time for ASL MRI. The advantages of DL techniques include fast computation time (i.e., nearly instantaneous once trained) and better retention of texture and resolution of the original images for the corresponding imaging modality. However, DL methods are highly dependent on the training datasets which may be specific to the imaging scanners and protocols used for data collection.

Recently, projection view-sharing techniques, such as "K-space Weighted Image Contrast" (KWIC) have been proposed to improve the spatial and temporal resolution of dynamic MRI with radial k-space trajectories, and to reduce the radiation dose of CTP scans while maintaining image temporal and spatial resolution. However, the main limitation is that these methods require specific pulse sequences with a predefined series of radial k-space trajectories for MRI and rapid-switching of pulsed X-ray at pre-specified rotation angles for CT. Both requiring specific modifications of MRI software and CT hardware that are not yet available on most clinical MRI and CT scanners.

The present disclosure introduces a new technique termed "K-space Weighted Image Average" (KWIA) that reduces the noise for perfusion imaging from medical imaging techniques including CTP, PET, SPECT, and MRI, which allows for using reduced X-ray radiation levels in CTP, reduced dose of radioactive tracers in PET/SPECT, reduced dose of GBCAs in DSC MRI and reduced scan time for ASL MRI. Compared to existing denoising (noise reduction) methods for perfusion imaging, the present disclosure has three principle advantages: (1) KWIA does not require modification of existing software or hardware of medical imaging scanners for raw data acquisition; (2) KWIA is computationally simple and fast (non-iterative), and therefore it does not affect clinical workflow; (3) KWIA preserves the texture as well as spatial and temporal resolution of the original images of the corresponding perfusion imaging modality.

2. Description of Embodiments

Figure 1:
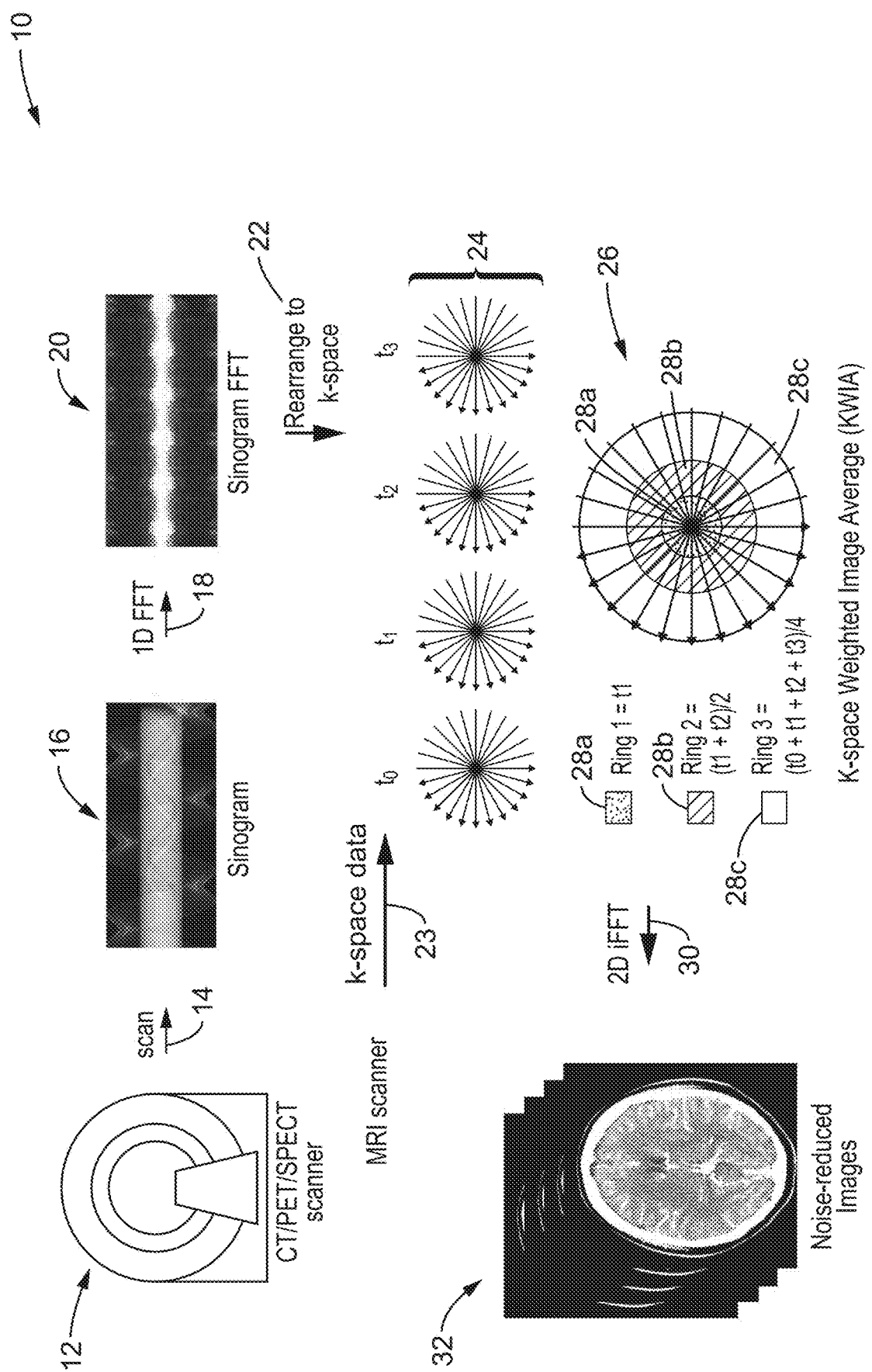
FIG. 1 is a block diagram of the KWIA method on raw projection or k-space data according to at least one embodiment of the present disclosure.

FIG. 1 illustrates an example embodiment 10 of performing k-space weighted image average (KWIA) according to the present description to provide reduced noise when dealing with reduced radiation doses in computed tomography perfusion (CTP), reduced doses of radioactive tracers in PET/SPECT and reduced doses of contrast agent in MRI. A CT, PET or SPECT device 12 performs a time series of scans 14 to generate a time series medical imaging data set exemplified here with sinogram 16. This data set can be related to the frequency domain through the central-slice theorem by performing 1-D Fourier transform (FT) 18 of the projection of an object into a sinogram FFT 20. This projection of the object is the same as the line drawn through the center of the 2-D FT plane (i.e., k-space). The FFT sinogram is then converted 22 into "k-space" data having a number of timeframes 24 (e.g., $t_0$, $t_1$, $t_2$ and $t_3$). View-shared averaging methods 26 are then applied to reduce noise and preserve high spatial and temporal resolutions of CTP, PET and SPECT data by progressively increasing the number of time frames for view-shared averaging for more distant regions of "k-space". It should be noted that to is a time frame index. The method preferably utilizes the center frame (instead of the first frame) as the main frame so that Ring 1 only uses data of t1. Ring 2 averages 2 frames t1 and t2. The more distant Ring 3 has a wider averaging window to include frames before and after t1 from t0 to t3. The figure depicts multiple rings, herein exemplified as 3 rings: Ring 1=$t_1$ 28a, Ring 2=$(t_1+t_2)/2$ 28b and Ring 3=$(t_0+t_1+t_2+t_3)/4$ 28c. A 2D inverse FFT is then performed 30 to produce a time series of noise reduced images 32. It should be appreciated that the methods of the present disclosure are in contrast to conventional KWIC CTP methods, which require pulsed X-ray images at specific rotation angles.

It should be appreciated that in the present disclosure "Rings" are referring to a geometrical region with a specific range of distance from the k-space center, where distance is defined by a mathematical formula such as L1-norm, L2-norm and infinity-norm distances, or similar formulas for defining regions with respect to distance. Thus, the "Rings" of the present disclosure are not limited to the specific geometries (e.g., circular, square, etc.) as seen in the depicted examples.

For MRI scanners, raw k-space data sets are directly output 23, to which view-shared averaging methods are then applied to reduce noise and preserve the spatial and temporal resolutions of the MRI data set by progressively increasing the number of time frames for view-shared averaging for more distant regions of "k-space". The methods of the present description are in contrast to conventional KWIC MRI methods, which require data acquisition with interleaved radial k-space trajectories according to a specific time series of projection angles. In contrast, the KWIA method can be applied to k-space data acquired with arbitrary trajectories, such as cartesian, radial, spiral and rosette patterns.

In the embodiment illustrated in FIG. 1, four timeframes of k-space data ($t_0$-$t_3$) are utilized by way of example and not limitation. Each 2D Fourier transform (FT) or k-space can be divided into multiple rings. The center region of k-space (Ring 1) utilizes data from only one time frame (t1) to maintain image contrast and temporal resolution of the original time series, while outer k-space regions will be averaged between neighboring time frames to reduce noise and increase SNR (e.g., Ring 2 can be averaged by 2 timeframes and Ring 3 averaged by 4 timeframes). Since the image contrast is primarily determined by the center k-space region, KWIA can preserve the spatial and temporal resolution and reduce the noise of CTP, PET, SPECT and MRI. The final noise-reduced images are obtained by applying inverse FFT on the KWIA filtered k-space data.

Figure 2:
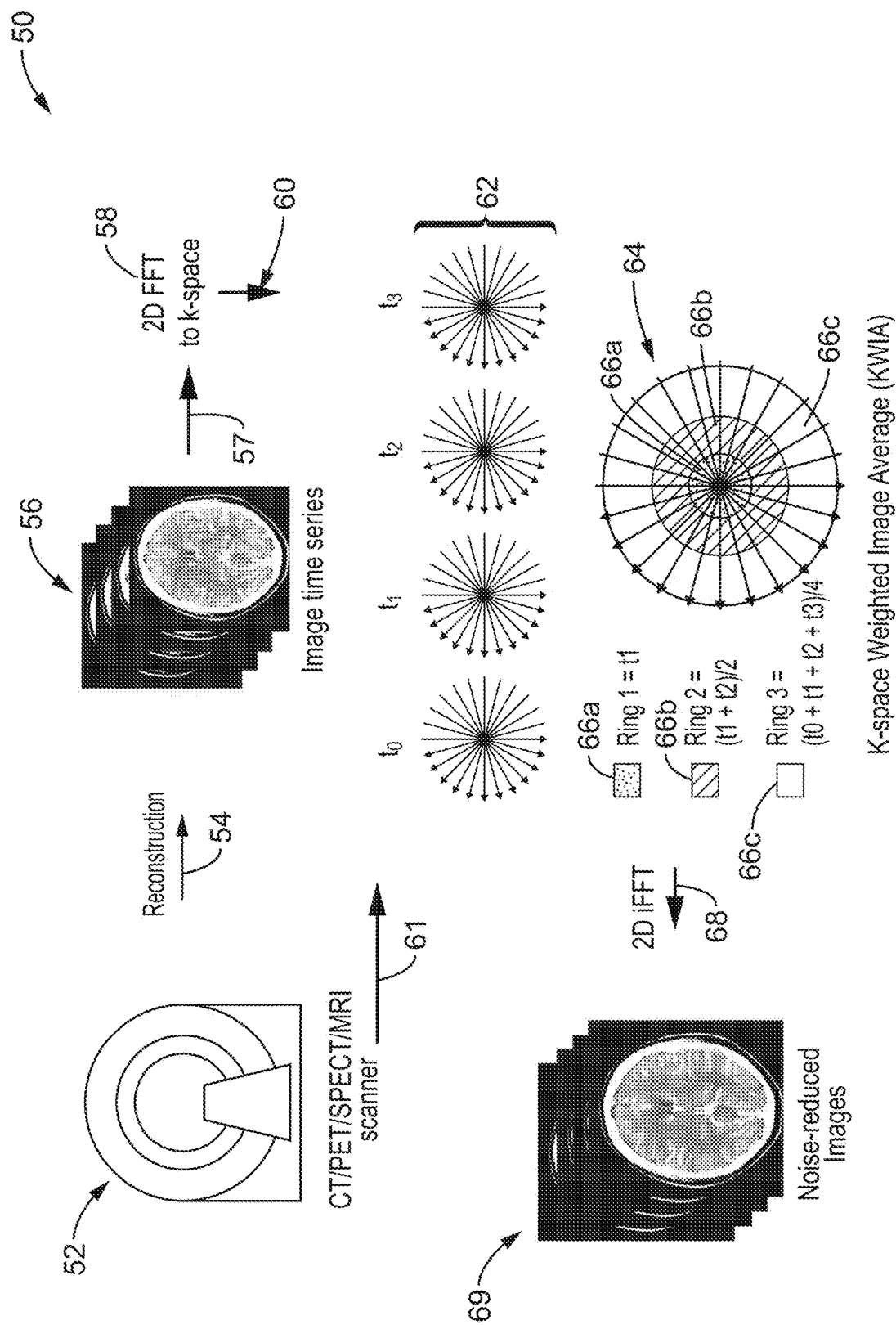
FIG. 2 is a block diagram of a variation of performing the KWIA method according to at least one embodiment of the present disclosure.

FIG. 2 illustrates another example embodiment 50 of a process for performing k-space weighted image average (KWIA) to reduce noise: (a) at lowered radiation doses in computed tomography perfusion (CTP), or (b) reduced dose of radioactive tracers in PET/SPECT, or (c) reduced dose of contrast agent in MRI according to the present disclosure.

A CTP, PET, SPECT or MRI device 52 performs a time series of scans which are reconstructed 54 using vendor software installed on the respective scanner, which may incorporate KWIA. The image time series 56 is then transformed 57 to the frequency domain, such as by performing 2-D Fourier transform (FT) 58 to convert the images into "k-space" data 60. The k-space data provides a series of timeframes 62 ($t_0$-$t_3$) to which view-shared averaging methods are applied 64 to reduce noise and preserve the spatial and temporal resolutions of CTP, PET, SPECT, and MRI data by progressively increasing the number of time frames for view-shared averaging for more distant regions of "k-space". The view-shared averaging is shown with multiple rings, exemplified as in FIG. 1 with 3 rings: Ring 1=$t_1$ 66a, Ring 2=$(t_1+t_2)/2$ 66b and Ring 3=$(t_0+t_1+t_2+t_3)/4$ 66c. An inverse FFT 68 is then applied on the KWIA filtered k-space data to produce a final time series of noise-reduced images 69.

The methods of the present disclosure are in contrast to conventional KWIC CTP and MRI methods, which require pulsed X-ray and radial projection trajectories at specific rotation angles, respectively. In contrast, the KWIA method can be applied on CTP, PET, SPECT, and MRI medical imaging data sets acquired with standard hardware and software.

Figure 3:
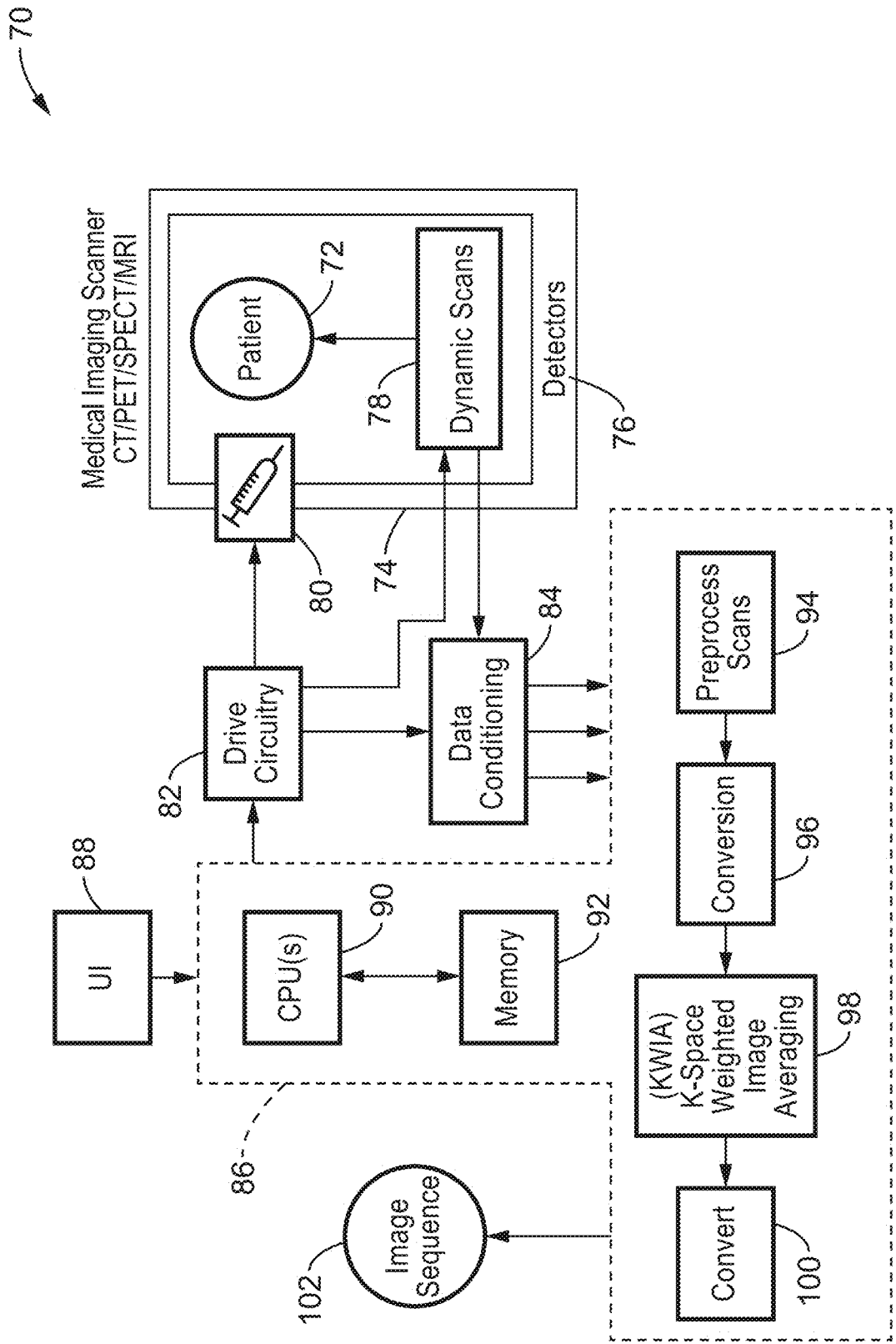
FIG. 3 is a block diagram of a medical imaging scanning system according to at least one embodiment of the present disclosure.

FIG. 3 illustrates an example embodiment 70 of a medical imaging scanning system (e.g., CTP, PET, SPECT or MRI) configured for generating a time series of medical data upon which the KWIA is performed. Each of these medical imaging techniques is configured for the present disclosure to provide dynamic scans on the same anatomical location to image dynamic signal changes caused by an exogenous contrast agent or radioactive tracer or an endogenous tracer like in ASL.

The system is configured for obtaining scan information from a patient 72 using a medical scanner 74 having one or more detectors 76, which is typically a plurality of detectors 76. The relationship between detectors and patient is generally adjusted to some anatomical location and the scans are commenced. A dynamic scans device 78 provides for motion correction during the scan, by adjusting the relative position between the patient, or a portion of the patient, and the detectors (e.g., adjusting either the patient position or the position of the detectors).

An injector 80 is configured for performing timed injection of a contrast agent or radioactive tracer, for Arterial Spin Labeling (ASL) this step is implemented using radiofrequency (RF) pulses to magnetically label arterial blood water as an endogenous tracer.

Drive circuitry 82 generates signals for controlling the operations of medical scanner 74, detectors 76, dynamic stage 78, injector 80, and other elements of the medical imaging system. Data is output from the detectors 76 to a data conditioning circuit 84. Data conditioning circuitry 84 is configured to condition the output from the medical imager 74, and in at least one embodiment comprises one or more amplifiers, filters, A/D converters or other circuits for preparing the signals and/or data set. It will be appreciated that data is generally also collected on the dynamic adjustment by the dynamic scan 78, and can include additional parameters such as the drive signals being sent by the drive circuitry, operation of injector 80, other measurements on or at the patient and other inputs as desired to allow properly interpreting scan data.

A processing section 86 is shown with one or more central processing units (CPUs) 90 and associated memory 92 which is non-transitory and configured for storing instructions executable by the processor, as well as any desired data. The processor, and its associated circuitry are configured to control the drive circuitry 82 receive data streams or sets from the data conditioning unit 84, and either directly or indirectly support a User Interface (UI) 88. Instructions executed by the processing section 86 are seen for processing the scan data by preprocessing 94, such as including motion compensation. Conversion 96 is performed, such as conversion to Fourier Transform (FT) or K-space conversion. After conversion the K-space Weighted Image Averaging (KWIA) 98 is performed, with output then converted 100 to images and output 102, or alternatively utilized as the basis for other processing within the system.

3. Processing Specifics

The Signal-to-Noise Ratio (SNR) of CT images is proportional to the square root of the X-ray tube current or radiation dose. The SNR of PET and SPECT is also proportional to the square root of the detected photon counts or dose of radiation tracers. Therefore, reducing the X-ray tube current of CTP scan or the dose of radioactive tracers in PET/SPECT by half will cause a $\sqrt{2}/2$ reduction in SNR. For MRI, reducing the dose of Gadolinium-Based Contrast Agents (GBCA) in Dynamic Susceptibility Contrast (DSC) MRI will result in decreased Contrast-to-Noise Ratio (CNR) since the change of relaxation rate (delta R2*) (note: R2* is gradient echo relaxation rate) is proportional to the dose of GBCA. Reduced scan time in Arterial Spin Labeling (ASL) MRI will also result in decreased SNR given that SNR is proportional to the square root of the measurement time.

The described KWIA method divides each 2D Fourier Transform (FT) or k-space data into multiple rings. The center region of k-space (Ring 1) directly utilizes the data from a single time frame (e.g., $t_1$ in FIG. 1), while outer k-space regions will be progressively averaged between neighboring time frames to reduce noise and increase SNR/CNR. By way of example and not limitation Ring 2 will be averaged by 2 timeframes $t_1$ and $t_2$, and Ring 3 will be averaged by 4 timeframes $t_0$ to $t_3$. Since the image contrast is primarily determined by the center k-space region and image details by the outer k-space, KWIA can preserve the spatial and temporal resolution while reducing noise and increasing SNR/CNR of CTP, PET and SPECT at reduced radiation doses, or DSC MRI with reduced dose of contrast agent and ASL MRI with reduced scan times.

An embodiment of a process to determine the radius or width of the rings in KWIA is given using projection data as an example. The center ring or R1 can be determined by the Nyquist criterion of projection data:

$$R1 = \frac{N_{proj} \cdot rSNR}{\pi}$$

where Nproj is the number of projections, and rSNR is relative SNR of low dose scan versus the full dose scan. The remainder of the k-space can be subsequently divided into rings that are progressively averaged between neighboring time frames to increase SNR. The radius of Ring n or Rn can be derived from the following $$Rn = R1 + \frac{\frac{Nres}{2} - R1}{Nrings - 1}(n-1)$$

where Nrings is the total number of rings, Nres is the image resolution, and Rn is the derived radius for the nth ring. In practice, the optimal number of rings and their respective sizes can be determined empirically. The more rings used, the higher the SNR. However, the resultant images will be more susceptible to potential motion as well as temporal smoothing (of fine structures) between time frames.

Figure 4A:
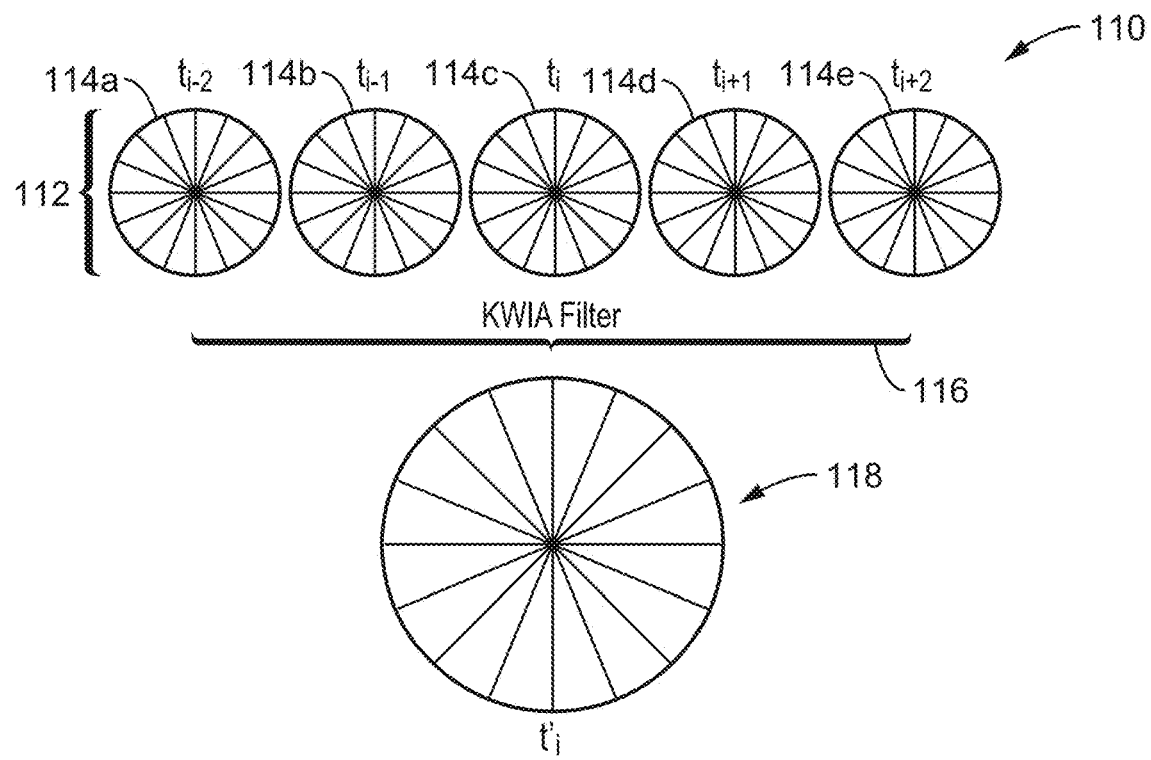
FIG. 4A through FIG. 4C are block diagrams of alternative KWIA filter configurations according to at least one embodiment of the present disclosure.
Figure 4B:
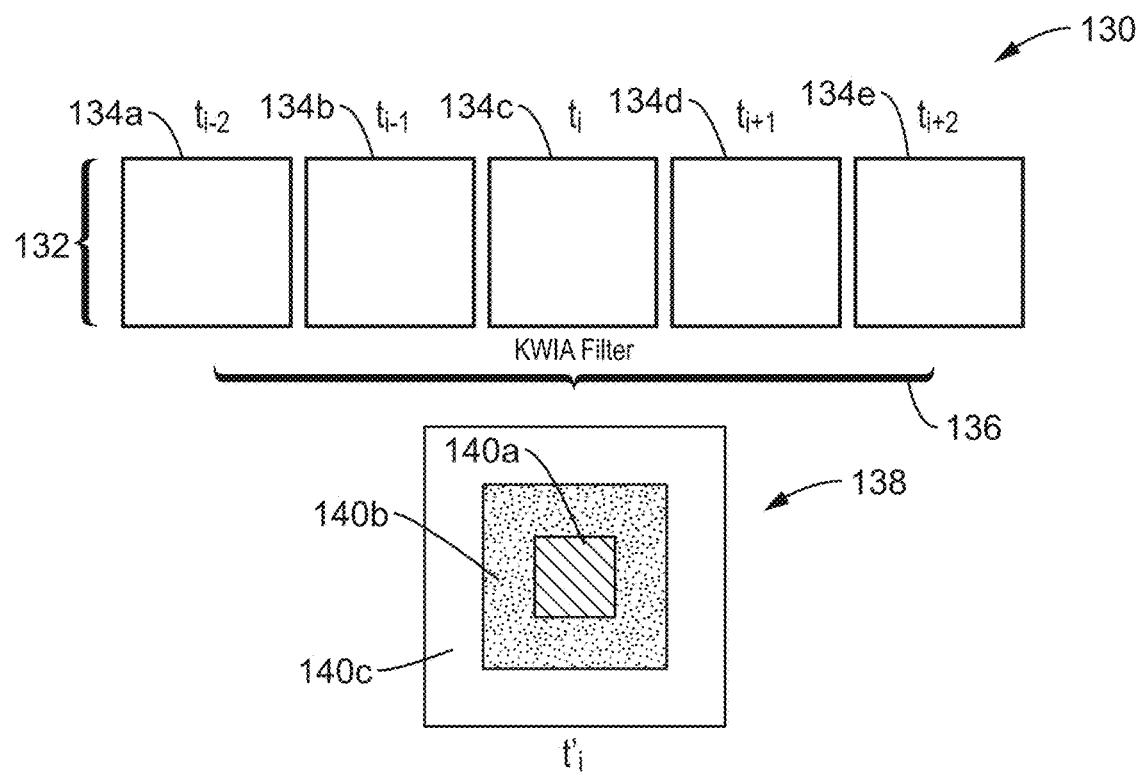
Figure 4C:
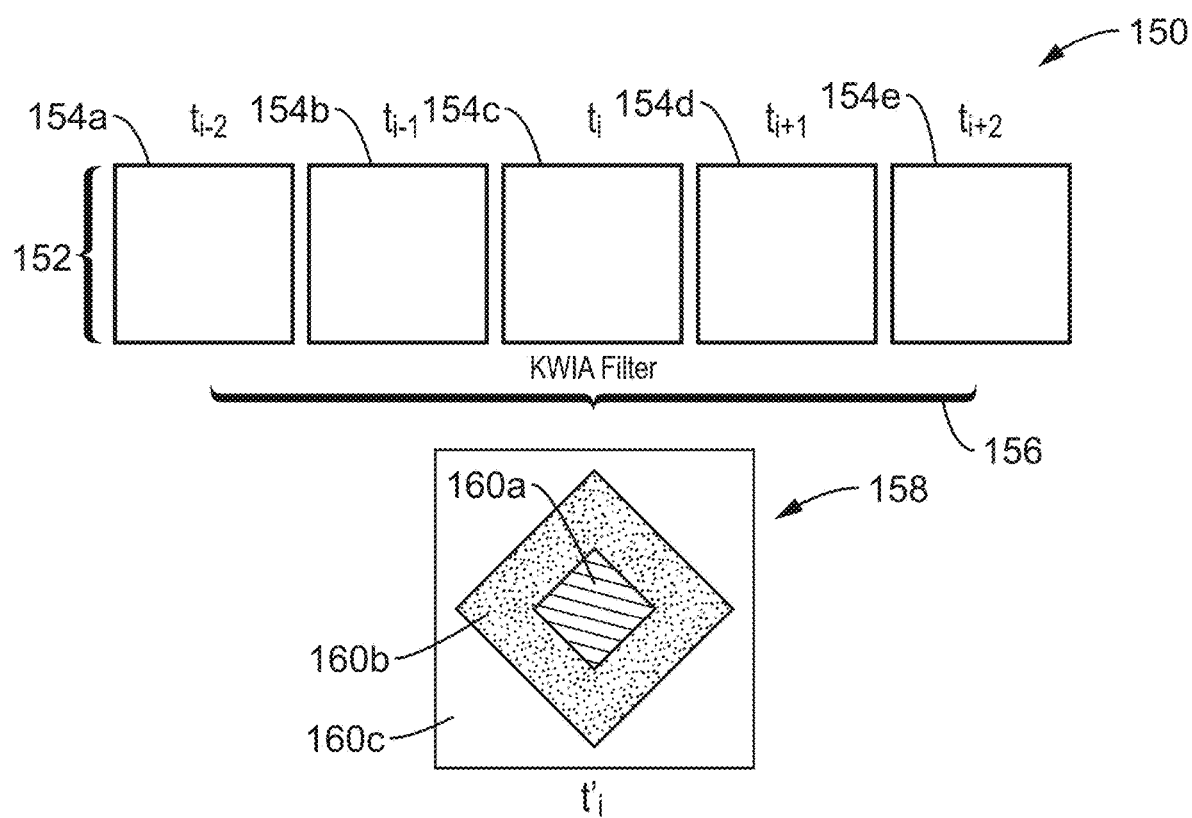

FIG. 4A through FIG. 4C illustrates example embodiments 110, 130 and 150 of different variations using a weighted k-space approach. In addition to dividing k-space into discrete rings, a weighted approach can be applied by which the k-space data is progressively averaged between neighboring time frames from the center towards outer k-space in a pseudo-continuous fashion.

In FIG. 4A is shown the KWIA filter 110 with continuously varying averaging window width shown with timeframes 112 (or fractions of timeframes, e.g., ½) from $t_{i-2}$ 114a, $t_{i-1}$ 114b, $t_i$ 114c, $t_{i+1}$ 114d and $t_{i+2}$ 114e which is proportional to the radial distance or L2 norm distance from the origin in k-space coordinate. At the k-space center, only data from the center timeframe $t_i$ 114c is used. With increasing radial distance from the k-space center, a wider window width is applied for averaging data from neighboring time frames. At the outermost circle of k-space, data from all 5 timeframes $t_{i-2}$ 114a, $t_{i-1}$ 114b, $t_i$ 114c, $t_{i+1}$ 114d and $t_{i+2}$ 114e are averaged. The KWIA filtered timeframe t 118 will have reduced noise, and the KWIA filter can be progressively applied to the full timeseries of images. Alternative KWIA filters can also be applied.

In FIG. 4B is shown the KWIA filter 130 with stepwise window width shown with timeframes 132 shown as $t_{i-2}$ 134a, $t_{i-1}$ 134b, $t_i$ 134c, $t_{i+1}$ 134d and $t_{i+2}$ 134e determined by the maximum norm distance (square) from the origin in k-space coordinate. The center square 140a only uses data from the center timeframe $t_i$ 134c. The region between the center and second squares 140b uses averaged data from three timeframes $t_{i-1}$ 134b, $t_i$ 134c, $t_{i+1}$ 134d. The region beyond the second square 140c uses averaged data from five timeframes $t_{i-2}$ 134a, $t_{i-1}$ 134b, $t_i$ 134c, $t_{i+1}$ 134d and $t_{i+2}$ 134e. The KWIA filtered timeframe t 138 will have reduced noise, and the KWIA filter can be progressively applied to the full timeseries of images.

In FIG. 4C is shown the KWIA filter 150 with stepwise averaging window width shown with timeframes 152 shown as $t_{i-2}$ 154a, $t_{i-1}$ 154b, $t_i$ 154c, $t_{i+1}$ 154d and $t_{i+2}$ 154e determined by the L1 norm distance (diamond) from the origin in k-space coordinate. The center diamond 160a only uses data from the center timeframe $t_i$ 154c. The region between the center and second diamonds 160b uses averaged data from three timeframes $t_{i-1}$ 154b, $t_i$ 154c, $t_{i+1}$ 154d. The region beyond the second diamond 160c uses averaged data from five timeframes $t_{i-2}$ 154a, $t_{i-1}$ 154b, $t_i$ 154c, $t_{i+1}$ 154d and $t_{i+2}$ 154e. The KWIA filtered timeframe t 158 provides reduced noise, and the KWIA filter can be progressively applied to the full timeseries of images.

The described KWIA system and method are applicable to 3D cone beam CT (CBCT), 3D PET/SPECT and 3D MRI acquisitions. Specifically, the central slice theorem for 3D geometry states that 1 D FFT of any 1 D Radon data of a 3D object, which can be obtained indirectly with Grangeat's method, is identical to the same radial line in the 3D k-space.

Therefore, 3D projection data can be converted to 3D k-space data which can be divided into multiple spherical shells or alternative patterns in 3D, such as seen in FIG. 4A through 4C, or other patterns without departing from the teachings of the present disclosure. KWIA can then be applied for view-shared averaging of more distant regions from the k-space center across the time frames of 3D images. Alternatively, for CBCT with circular geometry, where only the middle plane is defined by the X-ray source trajectory having a complete set of Radon data, approximate reconstruction can be applied on the projection data of the off-middle planes which can be converted to 3D k-space for KWIA processing.

The principle of the described KWIA method can also be applied in image space. For instance, one can apply a low or high-pass spatial frequency filter on the original images to separate the low and high spatial frequency components (i.e., corresponding to center and peripheral regions of k-space) respectively. The high spatial frequency components can then be averaged across neighboring time frames to reduce noise, as described in KWIA.

In a generally less preferred embodiment image domain filtering may be similarly applied, although it is less efficient than the described k-space methods.

The described KWIA method is applicable to dynamic CT, PET, SPECT and MRI imaging to measure physiological parameters other than perfusion, including but not limited to angiography, tracer binding potential, blood oxygenation, tissue metabolism and permeability of the Blood-Brain Barrier (BBB).

In addition to CT, PET, SPECT and MRI, the embodiment of KWIA processing shown in FIG. 2 is applicable to other imaging modalities, including but are not limited to ultrasound and optical imaging.

4. Results

Figure 5:
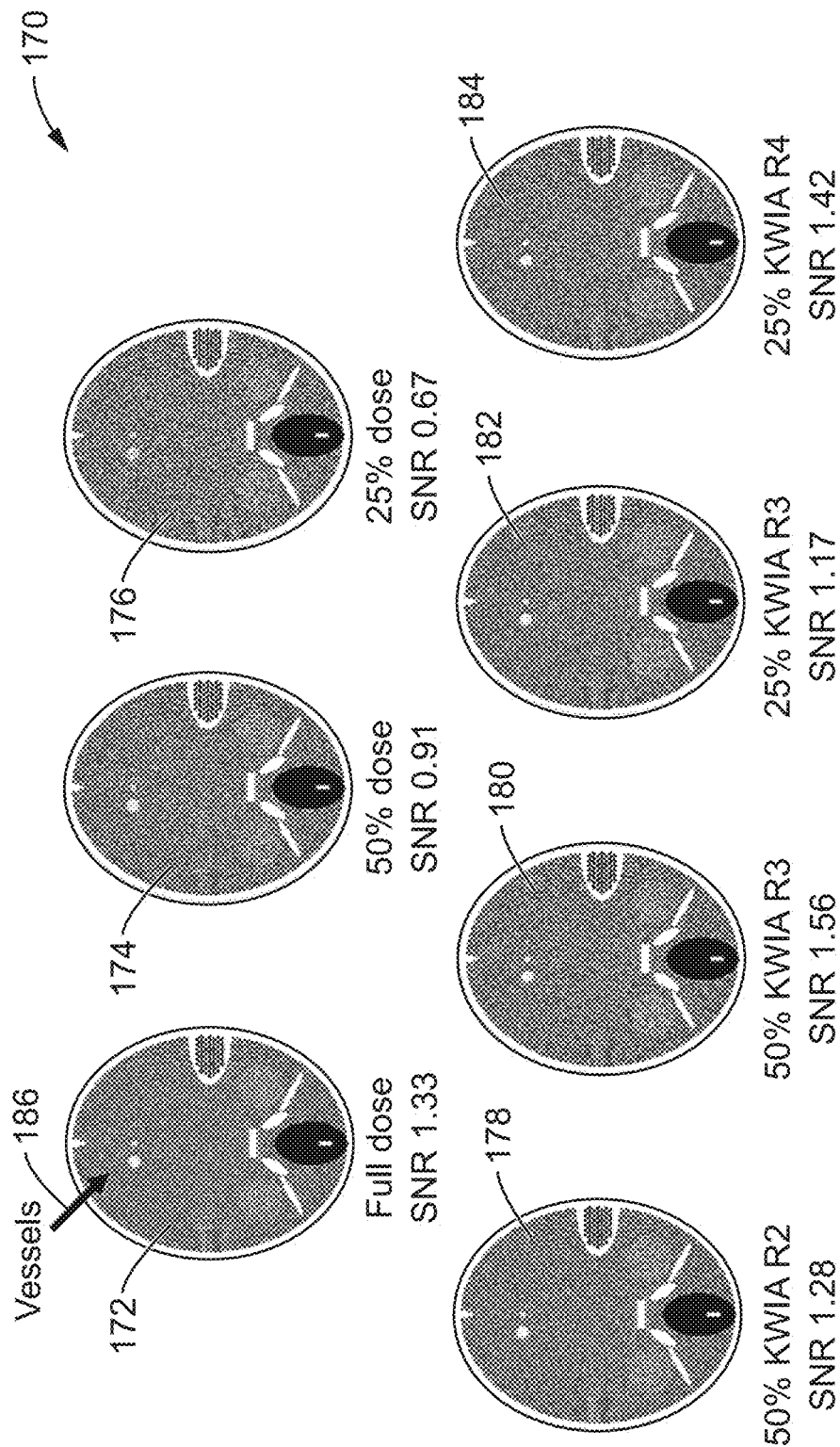
FIG. 5 are image results comparing the standard radial reconstruction and the KWIA method according to at least one embodiment of the present disclosure.

FIG. 5 illustrates example image results 170. The images were reconstructed with standard radial reconstruction (top image row) and the KWIA method with 2, 3 and 4 rings (KWIA R2, R3 and R4) respectively (bottom row). The corresponding signal-to-noise ratio (SNR) values are listed. Images 172, 174 and 176 depict simulated FORBILD digital phantom images with 100%, 50% and 25% radiation doses, with time-varying vessels 186 inserted (arrow). The respective SNR levels are seen as 1.33, 0.91 and 0.67.

In the lower portion of the figure images are seen 178, 180, 182 and 184 depicted at different dosage amounts 50% dose KWIA R2, 50% dose KWIA R3, 25% dose KWIA R3 and 25% dose KWIA R4 respectively. The respective image signal to noise ratios of these conversions are 1.28, 1.56, 1.17 and 1.42.

Poisson noise was added to the projection data of the FORBILD digital phantom to simulate radiation dose levels of 50% and 25% respectively, with time-varying vessels inserted, exemplified in image 172 showing arrow 186. The images were reconstructed with standard radial reconstruction and the KWIA method with 2, 3 and 4 rings respectively. As shown in the images of FIG. 5, utilizing KWIA with 3 and 4 rings can completely recover the SNR loss at 50% and 25% dose level respectively. Comparison between KWIA reconstructed images and full dose images illustrates that no structured noise pattern or texture changes were induced by KWIA reconstruction. The dynamic signals of the vessels with 10 mm and 5 mm sizes were reconstructed with filtered back projection (FBP) and KWIA respectively.

Figure 6A:
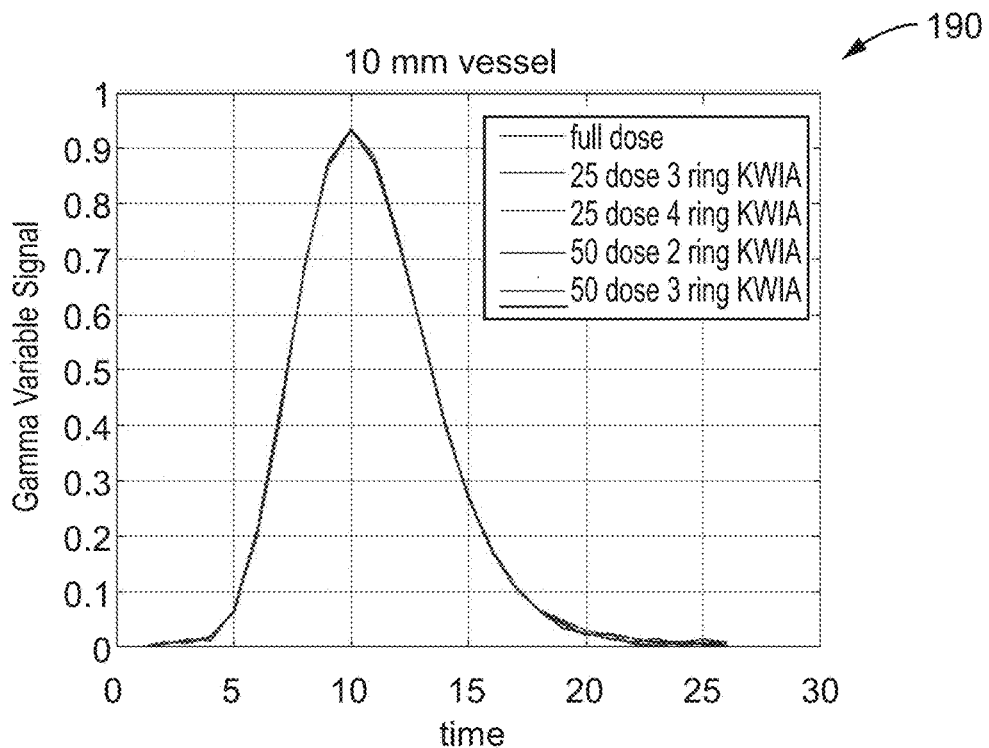
FIG. 6A and FIG. 6B are plots of dynamic signals from 10 mm and 5 mm vessels demonstrating that KWIA reconstruction according to at least one embodiment of the present disclosure doesn't adversely affect temporal parameters.
Figure 6B:
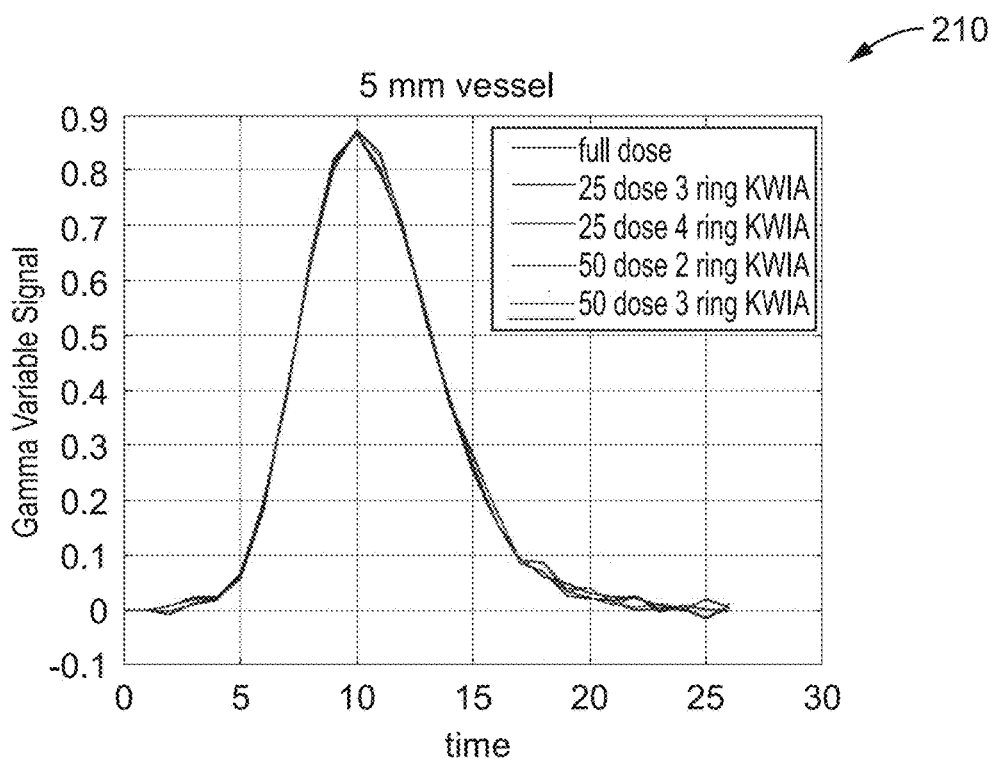

FIG. 6A and FIG. 6B illustrate 190, 210 that KWIA reconstruction of low dose CTP doesn't impact temporal parameters of the dynamic curves such as time-to-peak (TTP), area-under-the-curve (AUC) and full-width-at-half-maximum (FWHM). The figures depict plots of dynamic gamma variable signals with respect to time for 10 mm and a 5 mm vessel reconstructed with filtered back projection (FBP) and KWIA respectively. In each of these figures a gamma variable signal plot is seen at full dose, and KWIA reconstructions at 25% dose with 3 rings, 25% dose with 4 rings, 50% dose with 2 rings and 50% dose with 3 rings. These plots in each figure almost identically overlap which demonstrates that KWIA reconstruction doesn't affect the temporal parameters such as time-to-peak (TTP), area-under-the-curve (AUC) and full-width-at-half-maximum (FWHM).

FIG. 7 illustrates a comparison 230 of images at different dosage levels, with image insets showing a zoomed (magnified) region and information about the SNR changes for these regions. The top row of images depicts 232 clinical CTP data at 100% dose 232 and simulated (noise introduced) images at 50% 234 and 25% doses 236 respectively. The clinical CTP image and simulated images had SNRs and percentages of reduced SNR versus full dose SNR (as shown in parentheses) of 2.69, 1.88 with 69% of full dose SNR, and 1.32 with 49% of full dose SNR, respectively.

The images in the lower row of the figure were reconstructed with the KWIA method with 2, 3 and 4 rings (KWIA R2, R3 and R4) respectively. KWIA was able to completely recover SNR at 50% and 25% doses respectively. Comparison between magnified KWIA reconstructed images and full dose images illustrates that no structured noise pattern or texture changes were induced by KWIA reconstruction. The figure depicts an image reconstructed for a 50% dose using KWIA R2 238, a 50% dose using KWIA R3 240, a 25% dose using KWIA R3 242, and a 25% dose using KWIA R4 244. The respective SNRs and percentages of recovered SNR versus full dose SNR (as shown in parentheses) were 2.49 with 93% recovery, 2.88 with 107% recovery, 2.40 with 89% recovery and 2.79 with 104% recovery, which demonstrate very significant levels of recovery over the simulated results at the same dose levels.

FIG. 8A through FIG. 8D illustrate example results of arterial input function (AIF) 250, venous outflow function (VOF) 270 and tissue density signal (TDS) 290 as well as cerebral blood flow (CBF) maps 310 of 100% dose CTP data 312, and CTP data reconstructed with the KWIA methods at 50% dose 314 and 25% dose 316. These graphs show no significant differences between arterial input function (AIF), venous outflow function (VOF), tissue density signal (TDS) and calculated CBF maps of 100% dose CTP data, 50% and 25% dose CTP data reconstructed with the KWIA method with 3 and 4 rings (KWIA R3 and R4) respectively.

FIG. 9 illustrates example results of CTP phantom images acquired with actual 100% dose 332a with magnified view 332b, 60% dose 334a with magnified view 334b, and 30% dose 340a with magnified view 340b, as well as reduced dose scans reconstructed using KWIA with 2, 3 and 4 rings. The magnified view insets show a zoomed (magnified) region to demonstrate the SNR values and recovered percent SNR. The SNR for actual images is seen as 2.04 for 100% dose, SNR of 1.56 recovering 76% for the 60% dose, and SNR of 1.08 recovering 53% at 30% dose.

The SNR for KWIA reconstructions are shown at 60% dose with 2 rings 336a with magnified view 336b, at 60% dose with 3 rings 338a with magnified view 338b, at 30% dose with 3 rings 342a with magnified view 342b and at 30% dose with 4 rings 344a with magnified view 344b. The figure depicts corresponding SNR values and the recovered percentage SNR versus full dose (in parentheses). It is seen that KWIA with 3 and 4 rings was able to completely recover SNR at 60% and 30% doses respectively. The SNR values and recovered percent SNR are seen in the figures for KWIA recovered images providing an SNR of 2.06 recovering 101% for a 60% dose using 2 rings, an SNR of 2.40 recovering 118% for the 60% dose using 3 rings, an SNR of 1.82 recovering 89% at 30% dose using 3 rings, and an SNR of 2.11 recovering 103% for a 30% dose using 4 rings.

Comparison between magnified KWIA reconstructed images and full dose images illustrates that no structured noise pattern or texture changes were induced by KWIA reconstruction.

FIG. 10 illustrates example results 350 at 60% and 30% doses with plots of arterial input function (AIF) 352a, 354a, venous outflow function (VOF) 352b, 354b and tissue signals 352c, 354c. The left column depicts plots obtained at 60% and the right column plots obtained at 30%. Each plot contains results for CTP phantom data overlayed with results from KWIA reconstructed with differing numbers of rings (e.g., 2, 3 and 4 rings).

The plot curves overlap almost identically indicating that there are no significant differences between arterial input function (AIF), venous outflow function (VOF) and tissue signals between 60% and 30% dose CTP phantom data and those reconstructed with the KWIA methods respectively. These results are highly consistent with digital phantom and clinical CTP data with simulated low doses shown in the previous figures.

With the same implementation environment of MATLAB (Intel i5 CPU), it took 11.2 seconds for KWIA to reconstruct an image which was similar to the reconstruction time of 9.3 seconds required by industry standard method filter back projection (FBP). In comparison, iterative reconstruction took 265.8 seconds using MATLAB with a graphic processing unit (GTX 1660). An example of MATLAB code for implementing KWIA according to the presented technology is provided in Table 1.

5. Conclusions

The KWIA system and method of the present description preserves both spatial and temporal resolution, while reducing noise and enhancing image contrast for perfusion scans using CT, PET, SPECT, and MRI. The KWIA system and method allows the use of reduced X-ray radiation dose in CTP, reduced dose of radioactive tracers in PET/SPECT, reduced dose of GBCAs in DSC MRI and reduced scan time for ASL MRI. The method can be applied for perfusion imaging of body organs, multi-phase angiography, imaging tracer binding potential, blood oxygenation, tissue metabolism and vascular permeability of the brain and heart and other organs. The described KWIA method can also be directly applied on CTP, PET and SPECT data acquired with standard radiation dose as well as standard MRI to reduce noise and enhance image contrast.

6. General Scope of Embodiments

The enhancements described in the presented technology can be readily implemented within various medical imaging systems. It should also be appreciated that medical imaging system are preferably implemented to include one or more computer processor devices (e.g., CPU, microprocessor, microcontroller, computer enabled ASIC, etc.) and associated memory storing instructions (e.g., RAM, DRAM, NVRAM, FLASH, computer readable media, etc.) whereby programming (instructions) stored in the memory are executed on the processor to perform the steps of the various process methods described herein.

The computer and memory devices were not depicted in the diagrams for the sake of simplicity of illustration, as one of ordinary skill in the art recognizes the use of computer devices for carrying out steps involved with the processing of medical data into medical imaging. The presented technology is non-limiting with regard to memory and computer-readable media, insofar as these are non-transitory, and thus not constituting a transitory electronic signal.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, hardware processor, computer processor, central processing unit (CPU), and computer are used synonymously to denote a device capable of executing the instructions and communicating with input/output interfaces and/or peripheral devices, and that the terms processor, hardware processor, computer processor, CPU, and computer are intended to encompass single or multiple devices, single core and multicore devices, and variations thereof.

From the description herein, it will be appreciated that the present disclosure encompasses multiple embodiments which include, but are not limited to, the following:

1. An apparatus for reducing radiation dose during CT, comprising: (a) a CT scanner; (b) a processor configured to receive input from the CT scanner; and (c) a non-transitory memory storing instructions executable by the processor; (d) wherein said instructions, when executed by the processor, perform steps comprising: (d)(i) receiving a CT sinogram from the CT scanner; (d)(ii) converting the CT sinogram into k-space data; (d)(iii) performing projection view-sharing methods on the k-space data by progressively increasing the number of shared time frames for more distant regions of k-space; and (e) outputting a CT image at a decreased radiation dosage while preserving SNR and high-spatial and temporal resolutions.

2. A non-transitory medium storing instructions executable by a processor, said instructions when executed by the processor performing steps comprising: (a) receiving a CT sinogram from a CT scanner; (b) converting the CT sinogram into k-space data; (c) performing projection view-sharing methods on the k-space data by progressively increasing the number of shared time frames for more distant regions of k-space; and (d) outputting a CT image at a decreased radiation dosage while preserving SNR and high-spatial and temporal resolutions.

3. A method for reducing radiation dose during CT, the method comprising: (a) receiving a CT sinogram from a CT scanner; (b) converting the CT sinogram into k-space data; (c) performing projection view-sharing methods on the k-space data by progressively increasing the number of shared time frames for more distant regions of k-space; and (d) outputting a CT image at a decreased radiation dosage while preserving SNR and high-spatial and temporal resolutions; (e) wherein said method is performed by a processor executing instructions stored on a non-transitory medium.

4. An apparatus for reducing radiation dose and noise during CT, comprising: (a) a CT scanner; (b) a processor configured to receive input from the CT scanner; and (c) a non-transitory memory storing instructions executable by the processor; (d) wherein said instructions, when executed by the processor, perform steps comprising: (d)(i) receiving a CT sinogram or image from the CT scanner; (d)(ii) converting the CT sinogram or image into k-space data; (d)(iii) performing projection view-sharing methods on the k-space data by progressively increasing the number of shared time frames for more distant regions of k-space; and (e) outputting a CT image at a decreased or standard radiation dosage while increasing SNR and preserving high-spatial and temporal resolutions.

5. A non-transitory medium storing instructions executable by a processor, said instructions when executed by the processor performing steps comprising: (a) receiving a CT sinogram or image from a CT scanner; (b) converting the CT sinogram or image into k-space data; (c) performing projection view-sharing methods on the k-space data by progressively increasing the number of shared time frames for more distant regions of k-space; and (d) outputting a CT image at a decreased or standard radiation dosage while increasing SNR and preserving high-spatial and temporal resolutions.

6. A method for reducing radiation dose and noise during CT, the method comprising: (a) receiving a CT sinogram or image from a CT scanner; (b) converting the CT sinogram or image into k-space data; (c) performing projection view-sharing methods on the k-space data by progressively increasing the number of shared time frames for more distant regions of k-space; and (d) outputting a CT image at a decreased or standard radiation dosage while increasing SNR and preserving high-spatial and temporal resolutions; (e) wherein said method is performed by a processor executing instructions stored on a non-transitory medium.

7. An apparatus for reducing noise and radiation dose during dynamic CT, PET and SPECT scans comprising: (a) a CT, PET or SPECT scanner configured for generating a time series of scans on a specific anatomical location with scanning performed at a standard radiation dose or reduced radiation dose; (b) a processor configured to receive input from the CT, PET or SPECT scanner; and (c) a non-transitory memory storing instructions executable by the processor; (d) wherein said instructions, when executed by the processor, perform steps comprising: (d)(i) receiving scan data as a time series data set of dynamic CT, PET or SPECT sinogram or images from the CT, PET or SPECT scanner performing a scan; (d)(ii) converting the dynamic CT, PET or SPECT sinogram or images into k-space data having multiple time frames; (d)(iii) performing view-shared averaging methods on the k-space data by progressively increasing the number of shared time frames for more distant regions of k-space; and (e) outputting a sequence of CT, PET or SPECT images, which reduce noise and preserve spatial and temporal resolutions, regardless of whether the scan data was obtained at the standard or decreased radiation dosage.

8. An apparatus for reducing noise and dose of contrast agent or scan time for endogenous tracer during dynamic MRI scans comprising: (a) an MRI scanner configured for acquiring a time series of data on a specific anatomical location with scanning performed at a standard or reduced dose of contrast agent or scan time for endogenous tracer; (b) a processor configured to receive a time series input from the MRI scanner; and (c) a non-transitory memory storing instructions executable by the processor; (d) wherein said instructions, when executed by the processor, perform steps comprising: (d)(i) receiving scan data as a time series data set of dynamic MRI k-space data or images from the MRI scanner performing a scan; (d)(ii) converting the MRI images into k-space data; (d)(iii) performing view-shared averaging methods on the k-space data by progressively increasing the number of shared time frames for more distant regions of k-space; and (e) outputting a sequence of MRI images, which reduce noise and preserve spatial and temporal resolutions, regardless of whether the time series data set was obtained for the scan at the standard or decreased radiation dosage of contrast agent or scan time for endogenous tracer.

9. An apparatus for reducing noise and dose of contrast agent, radiation or scan time for endogenous tracer during dynamic CT, PET, SPECT and MRI scans comprising: (a) a CT, PET, SPECT or MRI scanner configured for acquiring a time series of data on a specific anatomical location with scanning performed at a standard or reduced dose of either radiation, contrast agent or scan time for endogenous tracer; (b) a processor configured to receive a time series input from the CT, PET, SPECT or MRI scanner; and (c) a non-transitory memory storing instructions executable by the processor; (d) wherein said instructions, when executed by the processor, perform steps comprising: (d)(i) receiving scan data as a time series data set from said CT, PET, SPECT or MRI scanner; (d)(ii) converting the time series data set from said CT, PET, SPECT or MRI scanner into k-space data; (d)(iii) performing view-shared averaging methods on the k-space data by progressively increasing the number of shared time frames for more distant regions of k-space; and (e) outputting a sequence of CT, PET, SPECT or MRI images, which reduce noise and preserve spatial and temporal resolutions, regardless of whether the time series data set was obtained for the scan at the standard or decreased dose.

10. A method for reducing noise and radiation dose, contrast agent or scan time during dynamic CT, PET, SPECT or MRI scans, the method comprising: (a) receiving scan data as a dynamic time series data set from said CT, PET, SPECT or MRI scanner for a specific anatomical location with scanning performed at a standard or reduced dose of either radiation, contrast agent or scan time for endogenous tracer; (b) converting the dynamic time series data into k-space data; (c) performing view-shared averaging methods on the k-space data by progressively increasing the number of shared time frames for more distant regions of k-space; and (d) outputting a sequence of CT, PET, SPECT or MRI images, which reduce noise and preserve spatial and temporal resolutions, regardless of whether the scan data was obtained at the standard or decreased dose level; (e) wherein said method is performed by a processor executing instructions stored on a non-transitory medium.

11. The apparatus, method or non-transitory medium storing instructions of any preceding claim, wherein said instructions when executed by the processor further perform steps comprising: performing k-space weighted image average (KWIA) to perform the projection view-sharing methods on the k-space data.

12. The apparatus, method or non-transitory medium storing instructions of any preceding claim, wherein a center of k-space is oversampled and interpolated to provide adequate SNR, and an outer k-space an averaged between neighboring time frames to increase SNR.

13. The apparatus, method or non-transitory medium storing instructions of any preceding claim, wherein image contrast is primarily determined by the k-space center and image details are primarily determined by the outer k-space.

14. The apparatus, method or non-transitory medium storing instructions of any preceding claim, wherein said time series data set comprises 2D or 3D time series data from the CT, PET or SPECT scanner.

15. The apparatus, method or non-transitory medium storing instructions of any preceding claim, wherein said instructions when executed by the processor further perform steps comprising: performing k-space weighted image averaging (KWIA) to perform the view-shared averaging methods on the k-space data.

16. The apparatus, method or non-transitory medium storing instructions of any preceding claim, wherein a center of k-space uses data from a single time frame to preserve the image contrast and temporal resolution and an outer k-space is averaged between neighboring time frames to reduce noise and increase SNR while preserving spatial resolution.

17. The apparatus, method or non-transitory medium storing instructions of any preceding claim, wherein image contrast is primarily determined by the k-space center and image details are primarily determined by the outer k-space.

18. The apparatus, method or non-transitory medium storing instructions of any preceding claim, wherein said k-space data has four or more timeframes.

19. The apparatus, method or non-transitory medium storing instructions of any preceding claim, wherein said CT, PET or SPECT scanner is further configured with an injector for injecting a contrast agent, or radioactive tracer, and wherein said instructions when executed by the processor further comprise controlling concurrent injections of a contrast agent, or radioactive tracer during said time series of scans.

20. The apparatus, method or non-transitory medium storing instructions of any preceding claim, wherein said instructions when executed by the processor are further configured for generating a reduced radiation dose by reducing X-ray tube current and/or voltage for CT, or reducing the dose of radioactive tracers for PET/SPECT.

21. The apparatus, method or non-transitory medium storing instructions of any preceding claim, wherein said time series data set comprises 2D or 3D time series data from the MRI scanner.

22. The apparatus, method or non-transitory medium storing instructions of any preceding claim, wherein said instructions when executed by the processor further perform steps comprising: performing k-space weighted image average (KWIA) to perform the view-shared averaging methods on the k-space data.

23. The apparatus, method or non-transitory medium storing instructions of any preceding claim, wherein a center of k-space uses data from a single time frame to preserve the image contrast and temporal resolution and an outer k-space is averaged between neighboring time frames to reduce noise and increase SNR while preserving spatial resolution.

24. The apparatus, method or non-transitory medium storing instructions of any preceding claim, wherein image contrast is primarily determined by the k-space center and image details are primarily determined by the outer k-space.

25. The apparatus, method or non-transitory medium storing instructions of any preceding claim, wherein said k-space data has four or more timeframes.

26. The apparatus, method or non-transitory medium storing instructions of any preceding claim, wherein said MRI scanner is configured with an injector for injecting contrast agent or using magnetic labeling during said time series of scans.

27. The apparatus, method or non-transitory medium storing instructions of any preceding claim, wherein said MRI scanner is configured for magnetic labeling performed to magnetically label arterial blood water as an endogenous tracer when performing Arterial Spin Labeling (ASL).

As used herein, the singular terms "a," "an," and "the" may include plural referents unless the context clearly dictates otherwise. Reference to an object in the singular is not intended to mean "one and only one" unless explicitly so stated, but rather "one or more."

Phrasing constructs, such as "A, B and/or C", within the present disclosure describe where either A, B, or C can be present, or any combination of items A, B and C. Phrasing constructs indicating, such as "at least one of" followed by listing group of elements, indicates that at least one of these group elements is present, which includes any possible combination of these listed elements as applicable.

References in this specification referring to "an embodiment", "at least one embodiment" or similar embodiment wording indicates that a particular feature, structure, or characteristic described in connection with a described embodiment is included in at least one embodiment of the present disclosure. Thus, these various embodiment phrases are not necessarily all referring to the same embodiment, or to a specific embodiment which differs from all the other embodiments being described. The embodiment phrasing should be construed to mean that the particular features, structures, or characteristics of a given embodiment may be combined in any suitable manner in one or more embodiments of the disclosed apparatus, system or method.

As used herein, the term "set" refers to a collection of one or more objects. Thus, for example, a set of objects can include a single object or multiple objects.

As used herein, the terms "approximately", "approximate", "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to +5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to 5°, less than or equal to 4°, less than or equal to 3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

Example of MATLAB code for Implementing KWIA Steps

```
% % % % % % % % % % % % % % % % % % % % % % % % % % % % % % % % % % % %
% % % % % % % % % % % % % % % % % % % % % % % % % % % % % % % %
% CT KWIA Reconstruction algorithm based on MRI KWIC Recon and CT KWIC
% This file is the main script for KWIA reconstruction
% It takes a series of CTP images from one CTP scan (27 images in our case)
% Transform it into projection data (728(#detectors)*576(#views)*27(#time
frames))
% Process the projections using KWIA filters
% Synthesize the KWIA projections
% Reconstruct images using Gridding Reconstruct
% Need add gridding in path
% % % % % % % % % % % % % % % % % % % % % % % % % % % % % % % % % % % %
% % % % % % % % % % % % % % % % % % % % % % % % % % % % % % % %
%% Setting Parameters
LD_path = './LD_sino/50_sino.mat';
DCM_path = './DICOM/'; % path of the folder containing original DICOM files of a
CTP scan
outpath = './KWIA_result/';
mkdir(outpath);
info_folder = dir(DCM_path); % DICOM folder
dose = 50; % 50 for 50% dose, 25 for 25% dose
ringNum = 3; % number of rings used for KWIA Recon, 2 or 3 used for 50% dose,
3 or 4 used for 25% dose
img_size = 512; % original image size
Nd = 728; % Detector numbers
view_total = 576; % projection numbers for 180 degree
dsRate = dose/100; % dose percentage
numSA = 2^(ringNum-1); % subapertures used for KWIA Recon
t_total = 27; % time frame numbers in a CTP scan
tube_angles_rad = linspace2(0,pi,view_total); %tube_angles, need ASTRA
shift = zeros(view_total,1); % shift of detector array
%% load sinogram of simulated low dose CTP images from one CTP scan
sino_stack = cell2mat(struct2cell(load(strcat(LD_path))));
%% Synthesizing KWIA projections
for imgNum = 1:t_total % for each time frame, 1st image will be the example
    fileName = info_folder(imgNum+2).name; % get the name of original DICOM
    info = dicominfo(strcat(DCM_path,fileName)); % load the DICOM header
    img_idx = line_calc(imgNum,1,view_total,t_total,numSA); % get indexes of
neighbor frames of the current frame, img_idx = [4,1,2,3], means the 1,2,3,4th
frames will be used.
    SA_sinos = sino_stack(:,:,img_idx); % load the sinogram of neighbor frames
    [ringArray] = get_ring_index(numSA,ringNum); % determine the ring indexes
that neighbor frames belongs to. ringArray = [3,1,2,3], which means 3 and 4th
frames belong to ring 2 and 3, frame 1 only belongs to ring 1, frame 2 only
belongs to ring 2.
        kdata_rad= zeros(Nd,view_total); % initial k space data
        for SA_idx = 1:numSA % for each neigbor frame
        sino = SA_sinos(:,:,SA_idx); % get sino for this neighor frame
        ring_idx = ringArray(SA_idx); % get the ring index of this neighbor frame
        [sino] = get_sino(sino,Nd,view_total); % move 1 pixel for each projection data
        k_sino = fftshift(fft(fftshift(sino))); % Take FFT on each projection data
        [k_sino_weighted,~] =
KWIC_average_weighting(k_sino,Nd,view_total,dsRate,ringNum,ring_idx); %
KWIC filter, averaging frames in outer rings.
```

TABLE 1-continued

Example of MATLAB code for Implementing KWIA Steps

```
    kdata_rad = kdata_rad + k_sino_weighted; % synthesize KWIA k space data
  end
  [u_rec,
kdata_cart]=Rad2Cart_voronoi_CT(kdata_rad,tube_angles_rad,shift,view_total,0,v
iew_total,0,1,1); % Gridding recon, u_rec will be Nd*Nd
  img_rec = ((flipud(u_rec(110:621,110:621 ))-u_water)./u_water).*1000; % crop
image to original size, and transfer to HU value
  % rescale img to be similar as original DICOM images, and save
  slope = 0.9121;
  intercept = -224.3766;
  img_rec2 = slope.*img_rec+intercept;
  info.RescaleIntercept = -3000;
dicomwrite(uint16(img_rec2+3000),strcat(outpath,fileName(1:2),'_KWIA_',string(d
ose),'_',string(ringNum),'Rings.dcm'),info);
  disp(strcat('finished_',string(imgNum)));
end
%% Function Called
function [sino_weighted,weight] =
KWIC_average_weighting(sino,Nd,view_total,dsRate,ringNum,ring_idx)
%KWIC_AVERAGE_WEIGHTING KWIA weighting for subapertures
if ringNum == 1
  sino_weighted = sino;
  weight = ones(size(sino));
else
  r_full = round(view_total/(pi/2)/2);
  r_1 = 1 *(r_full/sqrt(1/dsRate));
  r_rest = Nd/2-r_1;
  rjnterval = ceil(r_rest/(ringNum-1));
  r_ring = [-1 ,r_1 :r_interval:Nd/2];
  %r_ring = ([1:ringNum].*2-3).*(view_totardsRate)/pi;
  %r_ring = [-1,306];
  weight = zeros(Nd, 1);
  for j = 1:Nd
    r_current_point = abs(j-1-Nd/2);
    n = 1;
    if r_current_point > r_ring(end)
      weight(j) = 0.5 (ringNum-1);
    end
    while n <= ringNum
      if r_current_point <= r_ring(n)
        weight(j) = 0.5^(n-2);
        break;
      end
      n = n+1;
    end
  end
  for i = 1 :size(sino,2)
    for j = 1 :size(sino, 1)
      %if abs(j-1-Nd/2)<=(ring_idx*2-3).*(view_total*dsRate)/pi %ranges from
      if abs(j-1-Nd/2)<=r_ring(ring_idx) %ranges from
        sino(j,i)=0;
        sino(j,i)=0;
      end
    end
  end
  weight_mat = repmat(weight,[1,view_total]);
  sino_weighted = sino.*weight_mat;
end
end
```

What is claimed is:

1. An apparatus for reducing radiation dose and noise during CT, comprising:
(a) a CT scanner;
(b) a processor configured to receive input from the CT scanner; and
(c) a non-transitory memory storing instructions executable by the processor;
(d) wherein said instructions, when executed by the processor, perform steps comprising:
(i) receiving a CT sinogram or image from the CT scanner;
(ii) converting the CT sinogram or image into k-space data, wherein said k-space data comprises a plurality of timeframes $t_0, t_1, t_2, \ldots t_n$, and wherein $t_0$ is a time frame index;
(iii) performing projection view-sharing methods on the k-space data by progressively increasing the number of time frames for view-shared averaging for more distant regions of k-space, comprising
dividing the k-space into a center k-space region and a plurality of successive outer k-space regions,
wherein the center k-space region utilizes k-space data from only one time frame ($t_1$) to maintain image contrast and temporal resolution of said timeframes $t_0, t_1, t_2, \ldots t_n$, and progressively increasing the number of neighboring time frames for averaging outer k-space regions to reduce noise and increase SNR; and (e) outputting a CT image at a decreased or standard radiation dosage while increasing SNR and preserving high-spatial and temporal resolutions.

2. The apparatus of claim 1, wherein the center k-space region is oversampled and interpolated to provide adequate SNR, and wherein the outer k-space regions are progressively averaged between increasing neighboring time frames to increase SNR.

3. The apparatus of claim 2, wherein image contrast is primarily determined by the center k-space region and image details are primarily determined by the outer k-space regions.

4. The apparatus of claim 1, wherein said instructions when executed by the processor further perform steps comprising:
dividing the k-space into a center region, an outer region, and an outermost region;
the outer region averaging time frames $t_1$ and $t_2$;
the outermost region averaging time frames $t_0$ to $t_3$.

5. The apparatus of claim 4, wherein the center k-space region is oversampled and interpolated to provide adequate SNR, and wherein the outer k-space regions are progressively averaged between increasing neighboring time frames to increase SNR.

6. The apparatus of claim 5, wherein image contrast is primarily determined by the center k-space region and image details are primarily determined by the outer k-space regions.

7. An apparatus for reducing radiation dose and noise during CT, comprising:
(a) a CT scanner;
(b) a processor configured to receive input from the CT scanner; and
(c) a non-transitory memory storing instructions executable by the processor;
(d) wherein said instructions, when executed by the processor, perform steps comprising:

(i) receiving a CT sinogram or image from the CT scanner;
(ii) converting the CT sinogram or image into k-space data, wherein said k-space data comprises a plurality of timeframes $t_0, t_1, t_2, \ldots t_n$, and wherein $t_0$ is a time frame index;
(iii) performing projection view-sharing methods on the k-space data by progressively increasing the number of time frames for view-shared averaging for more distant regions of k-space, comprising
dividing the k-space into a center k-space region and a plurality of successive outer k-space regions,
wherein the center k-space region utilizes k-space data from only one time frame ($t_1$) to maintain image contrast and temporal resolution of said timeframes $t_0, t_1, t_2, \ldots t_n$,
progressively increasing the number of neighboring time frames for averaging outer k-space regions to reduce noise and increase SNR,
wherein the center k-space region is oversampled and interpolated to provide adequate SNR, and wherein the outer k-space regions are progressively averaged between increasing neighboring time frames to increase SNR,
wherein image contrast is primarily determined by the center k-space region and image details are primarily determined by the outer k-space regions; and
(e) outputting a CT image at a decreased or standard radiation dosage while increasing SNR and preserving high-spatial and temporal resolutions.

8. The apparatus of claim 7, wherein said instructions when executed by the processor further perform steps comprising:
dividing the k-space into a center region, an outer region, and an outermost region;
the outer region averaging time frames $t_1$ and $t_2$;
the outermost region averaging time frames $t_0$ to $t_3$.

* * * * *